United States Patent
Garg et al.

(10) Patent No.: US 12,201,694 B2
(45) Date of Patent: Jan. 21, 2025

(54) HYDROGEL COMPOSITIONS

(71) Applicants: Hyderabad Eye Institute, Hyderabad (IN); UNIVERSITY OF BRADFORD, Bradford (GB); UNIVERSITY OF SHEFFIELD, Sheffield (GB)

(72) Inventors: Prashant Garg, Hyderabad (IN); Stephen Rimmer, Bradford (GB); Charles William Ian Douglas, Sheffield (GB)

(73) Assignees: UNIVERSITY OF BRADFORD, Bradford (GB); UNIVERSITY OF SHEFFIELD, Sheffield (GB); HYDERABAD EYE INSTITUTE, Hyderabad (IN)

( * ) Notice: Subject to any disclaimer, the term of this patent is extended or adjusted under 35 U.S.C. 154(b) by 262 days.

(21) Appl. No.: 17/055,782

(22) PCT Filed: May 17, 2019

(86) PCT No.: PCT/GB2019/051367
§ 371 (c)(1),
(2) Date: Nov. 16, 2020

(87) PCT Pub. No.: WO2019/220136
PCT Pub. Date: Nov. 21, 2019

(65) Prior Publication Data
US 2021/0228735 A1 Jul. 29, 2021

(30) Foreign Application Priority Data

May 17, 2018 (IN) .............................. 201841018524
May 18, 2018 (IN) .............................. 201841018607

(51) Int. Cl.
| | |
|---|---|
| *A61K 47/69* | (2017.01) |
| *A61K 9/06* | (2006.01) |
| *A61K 31/7048* | (2006.01) |
| *A61K 31/785* | (2006.01) |
| *A61K 38/12* | (2006.01) |
| *A61K 38/14* | (2006.01) |
| *A61K 47/58* | (2017.01) |
| *A61P 31/10* | (2006.01) |
| *C12Q 1/04* | (2006.01) |

(52) U.S. Cl.
CPC ............ *A61K 47/6903* (2017.08); *A61K 9/06* (2013.01); *A61K 31/7048* (2013.01); *A61K 31/785* (2013.01); *A61K 38/12* (2013.01); *A61K 38/14* (2013.01); *A61K 47/58* (2017.08); *A61P 31/10* (2018.01); *C12Q 1/04* (2013.01)

(58) Field of Classification Search
CPC .. A61K 47/6903; A61K 9/06; A61K 31/7048; A61K 31/785; A61K 38/12; A61K 38/14; A61K 47/58; A61P 31/10; C12Q 1/04
See application file for complete search history.

(56) References Cited

U.S. PATENT DOCUMENTS

| | | | |
|---|---|---|---|
| 2011/0268807 A1* | 11/2011 | Su ........................ | A61K 9/0048 977/773 |
| 2013/0216600 A1 | 8/2013 | Da Silva Ferreira et al. | |
| 2021/0228734 A1* | 7/2021 | Garg ..................... | A61K 38/14 |

FOREIGN PATENT DOCUMENTS

| | | | | |
|---|---|---|---|---|
| WO | WO 2016/005288 | * | 1/2016 | ............. C08L 75/04 |
| WO | 2019/220136 A1 | | 11/2019 | |
| WO | 2019/220137 A1 | | 11/2019 | |

OTHER PUBLICATIONS

Qasim et al. (Macromolecular Research, vol. 22, No. 10, pp. 1125-1131 (2014) (Year: 2014).*
Lima et al. (Pharmaceutics 2020, 12, 970 pp. 2-28 p. 2 paragraph 3) (Year: 2020).*
Mesa-Arango et al., It only takes one to do many jobs: Amphotericin B as antifungal and immunomodulatory drug. Front Microbiol. Aug. 8, 2012;3:286, 10 pages.
Plenderleith et al., Highly-branched poly(N-isopropyl acrylamide)s with core-shell morphology below the lower critical solution temperature. RSC Advances. 2014;92:50932-7.
Te Welscher et al., Natamycin blocks fungal growth by binding specifically to ergosterol without permeabilizing the membrane. J Biol Chem. Mar. 7, 2008;283(10):6393-401.
Teratanatorn et al., Binding of Bacteria to Poly(N-isopropylacrylamide) Modified with Vancomycin: Comparison of Behavior of Linear and Highly Branched Polymers. Biomacromolecules. Sep. 11, 2017;18(9):2887-2899.
U.S. Appl. No. 17/055,768, filed Nov. 16, 2020, 2021-0228734, Published.
Rimmer et al., Highly branched poly-(N-isopropylacrylamide)s with arginine-glycine-aspartic acid (RGD)- or COOH-chain ends that form sub-micron stimulus-responsive particles above the critical solution temperature. Soft Matter. Jul. 17, 2007;3(8):971-973.
Tan et al., Characterization of a Polyethylene Glycol-Amphotericin B Conjugate Loaded with Free AMB for Improved Antifungal Efficacy. PLoS One. Mar. 23, 2016;11(3):e0152112, 18 pages.
Ansari et al., Current Thoughts in Fungal Keratitis: Diagnosis and Treatment. Curr Fungal Infect Rep. Sep. 1, 2013;7(3):209-218.
Doroshenko et al., Antibiotic functionalised polymers reduce bacterial biofilm and bioburden in a simulated Infection of the cornea. Biomater Sci. Jul. 24, 2018;6(8):2101-2109.
Hudson et al., Injectable in situ cross-linking hydrogels for local antifungal therapy. Biomaterials. Feb. 2010;31(6):1444-52.

(Continued)

*Primary Examiner* — Anna R Falkowitz
(74) *Attorney, Agent, or Firm* — McCarter & English, LLP; Steven G. Davis; Wei Song

(57) ABSTRACT

The present invention relates to hydrogel compositions comprising polymer conjugates capable of selectively binding to fungi, Gram positive bacteria and/or Gram negative bacteria. The hydrogel compositions can be used for detecting the presence of fungi, Gram positive bacteria and/or Gram negative bacteria in a sample.

16 Claims, 26 Drawing Sheets

(56) References Cited

OTHER PUBLICATIONS

Qasim et al., Enhanced Therapeutic Efficacy of Lipophilic Amphotericin B Against Candida albicans with Amphiphilic Poly (N-isopropylacrylamide) Nanogels. Macromolecular Research. 2014;22(10):1125-1131.
Ravicandran et al., Synthesis and evaluation of anti-fungal activities of sodium alginate-amphotericin B conjugates. Int J Biol Macromol. Mar. 2018;108:1101-1109.
Shepherd et al., Hyperbranched poly(NIPAM) polymers modified with antibiotics for the reduction of bacterial burden in infected human tissue engineered skin. Biomaterials. Jan. 2011;32(1):258-67.
Swift et al., Highly-branched poly(N-isopropyl acrylamide) functionalised with pendant Nile red and chain end vancomycin for the detection of Gram-positive bacteria. Acta Biomater. Mar. 15, 2019;87:197-206.
International Search Report and Written Opinion for Application No. PCT/GB2019/051367, dated Aug. 14, 2019, 15 pages.
International Search Report and Written Opinion for Application No. PCT/GB2019/051369, dated Aug. 14, 2019, 17 pages.
Sarker et al., Highly branched polymers with polymyxin end groups responsive to Pseudomonas aeruginosa. Biomacromolecules. Jan. 10, 2011;12(1):1-5.
Shepherd et al., Binding bacteria to highly branched poly(N-isopropyl acrylamide) modified with vancomycin induces the coil-to-globule transition. J Am Chem Soc. Feb. 17, 2010;132(6):1736-7.

* cited by examiner e)

HYDROGEL COMPOSITIONS

CROSS-REFERENCE TO RELATED APPLICATIONS

This application is a U.S. national stage filing, under 35 U.S.C. § 371 (c), of International Application No. PCT/GB2019/051367, filed on May 17, 2019, which claims priority to Indian Patent Application No. 201841018607, filed on May 18, 2018, and Indian Patent Application No. 201841018524, filed on May 17, 2018.

INTRODUCTION

The present invention relates to hydrogel compositions. More specifically, the present invention relates to hydrogel compositions comprising polymer conjugates that are capable of binding to fungi and Gram positive and/or Gram negative bacteria. The present invention also relates to the use of these hydrogel compositions for the detection of the presence of fungi, Gram positive and/or Gram negative bacteria in a sample, such as, for example, a biological sample.

BACKGROUND OF THE INVENTION

Many human and animal infections are caused by either Gram positive bacteria, Gram negative bacteria or fungi. In some instances, there may be more than one type of these pathogens present. To effectively treat an infection, it is important for clinicians to be able to quickly identify the cause, or likely cause, of the infection and initiate the appropriate antibiotic or antifungal treatment to eradicate the infection.

There is also a need for "portable" technologies, that can be used by clinicians in situations where there are no microbiology laboratory facilities readily available.

There is, therefore, a need for new techniques to help detect the presence of fungi, Gram positive bacteria and/or Gram negative bacteria in variety of different environments, including possible sites of infection on the human or animal body.

The present invention was devised with the foregoing in mind.

SUMMARY OF THE INVENTION

The present invention, in part, resides in the identification of certain novel polymer conjugates that comprise ligands capable of binding to ergosterol (a target of certain antifungal agents that resides on the surface of fungal cells). The ligands concerned are bound to a branched temperature-responsive polymer. The invention further resides in the recognition that these novel polymer conjugates can be formulated into a hydrogel composition in combination with polymer conjugates that are capable of binding to Gram positive bacteria and/or Gram negative bacteria.

Thus, according to a first aspect of the present invention there is provided a hydrogel composition comprising/consisting essentially of/consisting of a first polymer conjugate, or a salt thereof, having the general formula:

$$P\text{-}[Q]_x$$

wherein:
P is a branched temperature-responsive polymer comprising a plurality of functional groups, and wherein one or more of said functional groups are covalently attached to a ligand capable of binding to ergosterol;
Q is a ligand capable of binding to ergosterol; and
x is the percentage of functional groups on the branched temperature-responsive polymer, P, that are attached to Q, wherein x is greater than or equal to 10%;
together with:
(i) a second polymer conjugate, or a salt thereof, having the general formula:

$$P^1\text{-}[Q^1]_y$$

wherein:
$P^1$ is a branched temperature-responsive polymer, comprising a plurality of functional groups, and wherein one or more of said functional groups are covalently attached to a ligand capable of binding to Gram positive bacteria;
$Q^1$ is a ligand capable of binding to Gram positive bacteria; and
y is the percentage of functional groups on the branched temperature-responsive polymer, $P^1$, that are attached to $Q^1$, wherein y is greater than or equal to 10%; and/or
(ii) a third polymer conjugate, or a salt thereof, having the general formula:

$$P^2\text{-}[Q^9]_z$$

wherein:
$P^2$ is a branched temperature-responsive polymer, comprising a plurality of functional groups, and wherein one or more of said functional groups are covalently attached to a ligand capable of binding to Gram negative bacteria;
$Q^2$ is a ligand capable of binding to Gram negative bacteria; and
z is the percentage of functional groups on the branched temperature-responsive polymer, $P^2$, that are attached to $Q^2$, wherein z is greater than or equal to 10%.

According to a second aspect, there is provided a hydrogel composition comprising/consisting essentially of/consisting of hydrogel matrix, an aqueous medium (e.g. water) and a first polymer conjugate, or a salt thereof, having the general formula:

$$P\text{-}[Q]_x$$

wherein:
P is a branched temperature-responsive polymer comprising a plurality of functional groups, and wherein one or more of said functional groups are covalently attached to a ligand capable of binding to ergosterol;
Q is a ligand capable of binding to ergosterol; and
x is the percentage of functional groups on the branched temperature-responsive polymer, P, that are attached to Q, wherein x is greater than or equal to 10%;
together with:
(i) a second polymer conjugate, or a salt thereof, having the general formula:

$$P^1\text{-}[Q^1]_y$$

wherein:
$P^1$ is a branched temperature-responsive polymer comprising a plurality of functional groups, and wherein one or more of said functional groups are covalently attached to a ligand capable of binding to Gram positive bacteria;
$Q^1$ is a ligand capable of binding to Gram positive bacteria; and y is the percentage of functional groups on the branched temperature-responsive polymer, $P^1$, that are attached to $Q^1$, wherein y is greater than or equal to 10%;
and/or
(ii) a third polymer conjugate, or a salt thereof, having the general formula:

wherein:
$P^2$ is a branched temperature-responsive polymer comprising a plurality of functional groups, and wherein one or more of said functional groups are covalently attached to a ligand capable of binding to Gram negative bacteria;
$Q^2$ is a ligand capable of binding to Gram negative bacteria; and
z is the percentage of functional groups on the branched temperature-responsive polymer, $P^2$, that are attached to $Q^2$, wherein z is greater than or equal to 10%.

According to a third aspect, there is provided a contact lens comprising/consisting essentially of/consisting of a hydrogel composition as defined herein.

According to a fourth aspect of the present invention, there is provided a membrane, comprising/consisting essentially of/consisting of a hydrogel composition as defined herein.

According to a fifth aspect of the present invention, there is provided a swab comprising/consisting essentially of/consisting of a hydrogel composition as defined herein.

According to a sixth aspect of the present invention, there is provided a wound dressing comprising/consisting essentially of/consisting of a hydrogel composition as defined herein.

According to a seventh aspect of the present invention, there is provided a method of detecting the presence of fungi and Gram positive and/or Gram negative bacteria in a biological sample, the method comprising:
(i) contacting a hydrogel composition, contact lens, membrane, swab or wound dressing as defined herein with the biological sample;
(ii) removing the hydrogel composition, contact lens, membrane, swab or wound dressing as defined herein from the biological sample and testing the hydrogel composition, contact lens, membrane, swab or wound dressing for the presence of bound fungi and Gram positive and/or Gram negative bacteria.

According to an eighth aspect of the present invention, there is provided a method of determining the presence of a fungal infection and a Gram positive and/or Gram negative bacterial infection, the method comprising:
(i) contacting a hydrogel composition, contact lens, membrane, swab or wound dressing as defined herein with either a sample obtained from the suspected site of infection or with the suspected site of infection directly; and
(ii) removing the polymer conjugate, composition, hydrogel composition, contact lens, membrane, swab or wound dressing and determining whether any fungi and Gram positive and/or Gram negative bacteria are bound to the hydrogel composition, contact lens, membrane, swab or wound dressing respectively.

According to a ninth aspect of the present invention, there is provided a method of diagnosing the presence of a fungal infection, a Gram positive bacterial infection and/or a Gram negative bacterial infection, the method comprising:
(i) contacting a hydrogel composition, contact lens, membrane, swab or wound dressing as defined herein with either a sample obtained from the suspected site of infection or with the suspected site of infection directly;
(ii) removing the conjugate, composition, hydrogel composition, contact lens, membrane, swab or wound dressing;
(iii) determining whether any fungi, Gram positive and/or Gram negative bacteria are attached to the hydrogel composition, contact lens, membrane, swab or wound dressing; and
(iii) and optionally determining the particular species of fungi, Gram positive and/or Gram negative bacteria detected.

According to a tenth aspect of the present invention, there is provided the use of a hydrogel composition, contact lens, membrane, swab or wound dressing as defined herein for detecting the presence of fungi, Gram positive and/or Gram negative bacteria in a sample or for diagnosing a fungal, Gram positive bacteria and/or Gram negative bacterial infection.

DETAILED DESCRIPTION OF THE INVENTION

Definitions

Unless otherwise stated, the following terms used in the specification and claims have the following meanings set out below.

The term "temperature-responsive" is used herein to refer to polymers that undergo a temperature dependent change in hydration. The temperature at which a substantial change in polymeric hydration occurs is known as the critical solution temperature (CST). The lower critical solution temperature (LOST) is the critical temperature below which the copolymer becomes highly miscible with water and, in some cases, completely soluble. Above the LOST the copolymer is highly dehydrated and below the LOST the copolymer is highly hydrated. The term "temperature-responsive" is also used herein to refer to monomers which, when polymerised, form temperature-responsive polymers that undergo a temperature dependent change in hydration as discussed above.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups.

References to salts herein refer to any suitable salt forms of the polymer conjugates, including pharmaceutically acceptable salt forms. A suitable salt form of a polymer conjugate of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The Hydrogel Compositions of the Invention

The present invention relates to the preparation of hydrogel compositions comprising polymer conjugates capable of detecting fungi and Gram positive and/or Gram negative bacteria. The polymer conjugates comprise a branched temperature-responsive polymer and one or more ligands attached to the polymer that are capable of binding to ergosterol, which is present on the surface of fungi, or Gram positive bacteria or Gram negative bacteria.

The polymer conjugates that are capable of binding ergosterol present on the surface of fungal cells are novel materials. Ergosterol is a protovitamin found commonly within fungi and protozoan cell membranes.[1] Fungi cannot survive without ergosterol and it provides important physiological functions.[2] It therefore offers an enticing target for antifungal pharmacophores, such as for the antifungal drug amphotericin B (A-B).[3] The latter provides a common clinical treatment for fungal infections.[4] Although it is regularly used to treat severe fungal infections Amp-B is inherently toxic to host tissues.[5]. Recent attempts to optimise the delivery of amphotericin B and minimise toxicity have included attaching the drug to nanoparticles[6], detoxifying by delivery within polymer micellesm, improving solubility by conjugating it to PEG chain ends[8] and modifying the drug with sugar moieties.[9] The inventors found that the novel polymer conjugates used in the hydrogel composition of the present invention can effectively bind to fungi and they exhibit low toxicity. In particular, the inventors have found that the conjugates of poly(N-isopropylacrylamide) (or PNIPAM) with the antifungal agent amphotericin B bound thereto (described in the accompanying example section) exhibits low toxicity when compared to amphotericin B alone and retained the ability to bind to fungi. Thus, these novel polymer conjugates are suitable for selectively binding to fungi. They can be immobilised on a suitable support (such as, for example, hydrogel matrix, contact lens, swab, membrane, wound dressing etc.) and contacted with a sample to bind any fungi that are present in the sample. The presence, and optionally the identity, of the bound fungi can then be determined by conventional techniques known in the art, e.g. selective staining techniques, microscopy, culture and histological techniques. When bound to a hydrogel substrate the polymer conjugate functionalised with amphotericin B does not exhibit anti-fungal activity. However, surprisingly, such polymer conjugates are still able to bind to fungi and they exhibit low toxicity. Furthermore, the polymer conjugates of the present invention in which the ligand is an antifungal agent (e.g. amphotericin B) may also be used as novel antifungal agents by virtue of the retention of the antifungal activity and the low toxicity observed with the polymer conjugates.

As indicated above, the hydrogel compositions of the present invention comprise a first polymer conjugate, or a salt thereof, having the general formula:

$$P\text{-}[Q]_x$$

wherein:
P is a branched temperature-responsive polymer comprising a plurality of functional groups, and wherein one or more of said functional groups are covalently attached to a ligand capable of binding to ergosterol;
Q is a ligand capable of binding to ergosterol; and
x is the percentage of functional groups on the branched temperature-responsive polymer, P, that are attached to Q, wherein x is greater than or equal to 10%;

together with:
(i) a second polymer conjugate, or a salt thereof, having the general formula:

$$P^1\text{-}[Q^1]_y$$

wherein:
$P^1$ is a branched temperature-responsive polymer comprising a plurality of functional groups, and wherein one or more of said functional groups are covalently attached to a ligand capable of binding to Gram positive bacteria;
$Q^1$ is a ligand capable of binding to Gram positive bacteria; and
y is the percentage of functional groups on the branched temperature-responsive polymer, $P^1$, that are attached to $Q^1$, and wherein y is greater than or equal to 10%;

and/or
(ii) a third polymer conjugate, or a salt thereof, having the general formula:

$$P^2\text{-}[Q^2]_z$$

wherein:
$P^2$ is a branched temperature-responsive polymer comprising a plurality of functional groups, and wherein one or more of said functional groups are covalently attached to a ligand capable of binding to Gram negative bacteria;

$Q^2$ is a ligand capable of binding to Gram negative bacteria; and z is the percentage of functional groups on the branched temperature-responsive polymer, $P^2$, that are attached to $Q^2$, wherein z is greater than or equal to 10%.

In an embodiment, the hydrogel composition of the present invention comprises a first polymer conjugate of the formula $P\text{-}[Q]_x$ as defined herein, a second polymer conjugate of the formula $P^1\text{-}[Q^1]_y$ as defined herein, and a third polymer conjugate of the formula $P^2\text{-}[Q^2]_z$ as defined herein. These compositions are referred to herein as "triple hydrogels".

In an embodiment, the hydrogel composition of the present invention comprises a first polymer conjugate of the formula $P\text{-}[Q]_x$ as defined herein, and a second polymer conjugate of the formula $P^1\text{-}[Q^1]_y$ as defined herein, or a third polymer conjugate of the formula $P^2\text{-}[Q^2]_z$ as defined herein.

In another embodiment, the hydrogel composition of the present invention comprises a first polymer conjugate of the formula $P\text{-}[Q]_x$ as defined herein, and a second polymer conjugate of the formula $P^1\text{-}[Q^1]_y$ as defined herein, but the third polymer conjugate of the formula $P^2\text{-}[Q^2]_z$ as defined herein is not present.

In another embodiment, the hydrogel composition of the present invention comprises a first polymer conjugate of the formula $P\text{-}[Q]_x$ as defined herein, and a third polymer conjugate of the formula $P^2\text{-}[Q^2]_z$ as defined herein, but the second polymer conjugate of the formula $P^1\text{-}[Q^1]_y$ as defined herein is not present.

The ligand capable of binding to ergosterol, Q, may be any suitable ligand known in the art that can bind to ergosterol. Suitably, Q is a low molecular weight compound having a molecular weight of less than 1400 or less than 1200 Daltons. More typically, the ligand capable of binding to ergosterol, Q, will be a compound with a molecular weight of less than 1000 Daltons In an embodiment of the invention, Q is an antifungal agent that is capable of binding to ergosterol. In another embodiment, Q is amphotericin B, nystatin or natamycin. In a further embodiment, Q is amphotericin B.

The ligand $Q^1$ may be any suitable ligand known in the art that can bind to Gram positive bacteria such as dalbavancin, daptomycin, oritavancin or telavancin. Suitably, $Q^1$ is a small molecular weight compound having a molecular weight of less than 1500 Daltons.

In an embodiment of the invention, $Q^1$ is an antibacterial agent that is capable of binding to the surface of Gram positive bacteria. Suitably, $Q^1$ is vancomycin or a derivative thereof. Suitable derivatives of vancomycin will be well known to those skilled in the art. Non-limiting examples of derivatives of vancomycin are described in Allen et al.[10] Examples of other proposed structures are disclosed in Lueng et al.[11]

In an embodiment, $Q^1$ is vancomycin.

The ligand $Q^2$ may be any suitable ligand known in the art that can bind to Gram negative bacteria. Suitably, $Q^2$ is a small molecular weight compound having a molecular weight of less than 1500 Daltons.

In an embodiment of the invention, $Q^2$ is an antibacterial agent that is capable of binding to the surface of Gram negative bacteria. In a particular embodiment, $Q^2$ is polymyxin B.

Alternatively, $Q^2$ is polymyxin B derivative capable of binding to lipopolysaccharides, such as those described but not limited by Magee et al.[12] or Vaara.[13]

It will be appreciated that the functional groups of each branched temperature-responsive polymer (i.e. P, $P^1$ or $P^2$) may comprise any suitable chemical functional group that is capable of forming a covalent attachment with the ligand associated therewith (i.e. Q, $Q^1$ or $Q^2$ respectively). In an embodiment, the functional groups of P, $P^1$ or $P^2$ are independently selected from amino, hydroxy, alkenyl, alkynyl, acyl, sulfonyl, sulfinyl, mercapto, azido, ester, isocyanate and/or carboxyl groups. In another embodiment, the functional groups of P, $P^1$ or $P^2$ are independently selected from hydroxy, acyl, sulfonyl, sulfinyl, ester and/or carboxyl groups. In another embodiment, the functional groups of P, $P^1$ or $P^2$ are independently selected from sulfonyl, ester and/or carboxyl groups. In yet another embodiment, the functional groups of P, $P^1$ or $P^2$ are independently selected form carboxyl and/or ester groups. In still a further embodiment, the functional groups of P, $P^1$ or $P^2$ are carboxyl groups.

Suitably, the ester groups of the functional groups of P, $P^1$ or $P^2$ as detailed above are succinimide esters groups (i.e. N-hydroxysuccinimide (NHS) or N-hydroxysulfosuccinimide (Sulfo-NHS) activated esters).

It will be understood that the term "plurality of functional groups" refers to two or more functional groups.

It will also be appreciated that the functional groups of each branched temperature-responsive polymer (i.e. P, $P^1$ or $P^2$) may be located at any position of the respective branched temperature-responsive polymer. In an embodiment, the functional groups of each branched temperature-responsive polymer (i.e. P, $P^1$ or $P^2$) are located at, or near, (preferably at) the terminal end (terminus) of each branch of the branched temperature-responsive polymer. Thus, in an embodiment, the functional groups may be said to be "terminal functional groups".

The ligands Q, $Q^1$ or $Q^2$ may be bound to one or more functional groups of the respective branched temperature-responsive polymers, P, $P^1$ or $P^2$, by any suitable linkage. In an embodiment, each ligand Q, $Q^1$ or $Q^2$ is covalently bound to one or more functional groups on the respective branched temperature-responsive polymer P, $P^1$ or $P^2$.

Suitably, each Q, $Q^1$ or $Q^2$ present is bound to a (terminus) of one of the branches of the respective branched temperature-responsive polymer, P, $P^1$ or $P^2$, by the reaction of a (terminal) functional group present on P, $P^1$ or $P^2$ with a functional group present on Q, $Q^1$ or $Q^2$ to form one of the following linking groups:
—$NR_1$—, —O—, —C(O)—O—, —O—C(O)—, —N($R_1$)C(O)O—, —O(O)CN($R_1$)—, —S—, —S(O)—, —S(O)$_2$—, —S(O)$_2$—$NR^1$, —$NR^1$—S(O)$_2$— or a triazole linking group (formed by "click" chemistry), wherein $R_1$ is hydrogen or (1-4C)alkyl (e.g. methyl).

In an embodiment, each Q, $Q^1$ or $Q^2$ present is bound to a (terminus) of one of the branches of the respective branched temperature-responsive polymer, P, $P^1$ or $P^2$, by the reaction of a (terminal) functional group present on P, $P^1$ or $P^2$ with a functional group present on Q, $Q^1$ or $Q^2$ to form one of the following linking groups:
—C(O)—O—, —O—C(O)—, —N($R_1$)C(O)O—, —O(O)CN($R_1$)—, —S(O)—, —S(O)$_2$—, —S(O)$_2$—$NR_1$, —$NR^1$—S(O)$_2$— or a triazole linking group (formed by "click" chemistry), wherein $R_1$ is hydrogen or (1-4C)alkyl (e.g. methyl).

In another embodiment, each Q, $Q^1$ or $Q^2$ present is bound to a (terminus) of one of the branches of the respective branched temperature-responsive polymer, P, $P^1$ or $P^2$, by the reaction of a (terminal) functional group present on P, $P^1$ or $P^2$ with a functional group present on Q, $Q^1$ or $Q^2$ to form one of the following linking groups:
—C(O)—$NR_1$—, —$NR_1$—C(O)—, —S(O)$_2$—$NR^1$ or —$NR_1$—S(O)$_2$—, wherein $R_1$ is hydrogen or (1-4C) alkyl (e.g. methyl).

Suitable chemical techniques for forming the above linking groups are well-known in the art.

In an embodiment, each Q, $Q^1$ or $Q^2$ present is bound to a (terminus) of one of the branches of the respective branched temperature-responsive polymer, P, $P^1$ or $P^2$, by reaction of a (terminal) functional group present on P, $P^1$ or $P^2$ with a functional group present on Q, $Q^1$ or $Q^2$ to form a —C(O)—NH— linking group. Suitably, each Q, $Q^1$ or $Q^2$ present is bound to a (terminus) of one of the branches of the respective branched temperature-responsive polymer, P, $P^1$ or $P^2$, by reaction of a (terminal) carboxyl and/or ester group present on P, $P^1$ or $P^2$ with an amino group present on Q, $Q^1$ or $Q^2$ to form a —C(O)—NH— linking group. Most suitably, each Q, $Q^1$ or $Q^2$ present is bound to a (terminus) of one of the branches of the respective branched temperature-responsive polymer, P, $P^1$ or $P^2$, by reaction of a (terminal) carboxyl group present on P, $P^1$ or $P^2$ with an amino group present on Q, $Q^1$ or $Q^2$ to form a —C(O)—NH— linking group.

It will also be understood that for a given branched temperature-responsive polymer (i.e. P, $P^1$ or $P^2$) there will be a maximum theoretical number of (terminal) functional groups available for covalent attachment to Q, $Q^1$ or $Q^2$ respectively. In each case, the actual mean number (or percentage) of ligands Q, $Q^1$ or $Q^2$ that are attached to the (terminal) functional groups of the branched temperature-responsive polymers, P, $P^1$ or $P^2$, may be determined using any suitable means known in the art (e.g. $^1$H-NMR, UV spectroscopy and/or infrared spectroscopy).

The actual mean number of ligands Q, $Q^1$ or $Q^2$, that are attached to the (terminal) functional groups of the branched temperature-responsive polymers P, $P^1$ or $P^2$ respectively, may therefore be expressed as a percentage (or fraction) of the maximum theoretical number of (terminal) functional groups. As described hereinabove, x, y and z define the percentage of functional groups on the respective branched temperature-responsive polymers, P, $P^1$ or $P^2$, that are attached to corresponding ligands Q, $Q^1$ or $Q^2$.

In an embodiment, each of x, y and z are independently greater than or equal to 20%. Suitably, each of x, y and z are independently greater than or equal to 30%. More suitably, each of x, y and z are independently greater than or equal to 40%. Yet more suitably, each of x, y and z are independently greater than or equal to 50%. Even more suitably, each of x, y and z are independently greater than or equal to 60%. Still more suitable, each of x, y and z are independently greater than or equal to 70%. Further suitably, each of x, y and z are independently greater than or equal to 80%. Even further suitably, each of x, y and z are independently greater than or equal to 90%. Most suitably, each of x, y and z are independently greater than or equal to 95%.

In another embodiment, each of x, y and z are independently selected from a percentage between 10% and 99%. Suitably, each of x, y and z are independently selected from a percentage between 20% and 99%. More suitably, each of x, y and z are independently selected from a percentage between 30% and 99%. Even more suitably, each of x, y and z are independently selected from a percentage between 40% and 99%. Still more suitably, each of x, y and z are independently selected from a percentage between 50% and 99%. Yet more suitably, each of x, y and z are independently selected from a percentage between 60% and 99%. Further suitably, each of x, y and z are independently selected from a percentage between 70% and 99%. Most suitably, each of x, y and z are independently selected from a percentage between 80% and 99%

Thus, in an embodiment, at least 20% of the total (terminal) functional groups present on each branched temperature-responsive polymer, P, $P^1$ or $P^2$, are attached to ligands Q, $Q^1$ or $Q^2$ respectively. Suitably, at least 30% of the total (terminal) functional groups present on each branched temperature-responsive polymer, P, $P^1$ or $P^2$, are attached to ligands Q, $Q^1$ or $Q^2$ respectively. More suitably, at least 40% of the total (terminal) functional groups present on each branched temperature-responsive polymer, P, $P^1$ or $P^2$, are attached to ligands Q, $Q^1$ or $Q^2$ respectively. Even more suitably, at least 50% of total (terminal) functional groups present on each branched temperature-responsive polymer, P, $P^1$ or $P^2$, are attached to ligands Q, $Q^1$ or $Q^2$ respectively. Still more suitably, at least 60% of the total (terminal) functional groups present on each branched temperature-responsive polymer, P, $P^1$ or $P^2$, are attached to ligands Q, $Q^1$ or $Q^2$ respectively. Yet more suitably, at least 70% of the total (terminal) functional groups present on each branched temperature-responsive polymer, P, $P^1$ or $P^2$, are attached to ligands Q, $Q^1$ or $Q^2$ respectively. Further suitably, at least 80% of the total (terminal) functional groups present on each branched temperature-responsive polymer, P, $P^1$ or $P^2$, are attached to ligands Q, $Q^1$ or $Q^2$ respectively. Still further suitably, at least 90% of the total (terminal) functional groups present on each branched temperature-responsive polymer, P, $P^1$ or $P^2$, are attached to ligands Q, $Q^1$ or $Q^2$ respectively. Most suitably, at least 95% of the total (terminal) functional groups present on each branched temperature-responsive polymer, P, $P^1$ or $P^2$, are attached to ligands Q, $Q^1$ or $Q^2$ respectively.

In an embodiment, all of the of the (terminal) functional groups present on each branched temperature-responsive polymer, P, $P^1$ or $P^2$, are attached to ligands Q, $Q^1$ or $Q^2$ respectively.

The branched temperature-responsive polymer P, $P^1$ or $P^2$ may be any suitable branched temperature-responsive polymer known in the art.

Branched polymers are commonly defined by their degree of branching (DB), together with their molar masses. The degree of branching (DB) of the branched temperature-responsive polymer is commonly approximated using the following equation:

DB=number of branch points/number of polymer repeat units.

Thus, in embodiments where the branched temperature-responsive polymer terminates in a single functional group (i.e. no bi- or multi-molecular termination is present), each functional group corresponds to a branch of the polymer. Thus, the following approximation may be used to calculate the degree of branching of the branched temperature-responsive polymers of the present invention:

number of branch points/number of repeat units≈the number of end groups/number of repeat units.

Thus, in certain embodiments, and using the above approximations, the degree of branching (DB) of the branched temperature-responsive polymers, P, $P^1$ or $P^2$, may said to be between 0.01 and 0.5. In other embodiments, the degree of branching (DB) of the branched temperature-responsive polymers, P, $P^1$ or $P^2$, may be said to be between 0.01 and 0.2. In further embodiments, the degree of branching (DB) of the branched temperature-responsive polymers, P, P¹ or P², may be said to be between 0.02 and 0.01. In yet further embodiments, the degree of branching (DB) of the branched temperature-responsive polymers, P, P¹ or P², may be said to be between 0.03 and 0.1.

Suitable branched temperature-responsive polymers P, P¹ or P² of the present invention have a lower critical solution temperature (LOST) within the range of 5° C. to 70° C. In an embodiment, each of P, P¹ or P² has a LOST within the range of 15° C. to 40° C. or 25° C. to 35° C.

In addition to temperature-dependent changes in hydration, certain polymers P, P¹ or P² of the present invention (e.g. PNIPAM) may also undergo a full or partial desolvation upon binding of the Q to ergosterol present on a fungal cell, Q¹ to a Gram positive bacterial cell and Q² to a Gram negative bacterial cell. Without wishing to be bound by any particular theory, it is believed that this change in conformation results in the polymer adopting a more desolvated/globular form which in turn could lead to a further increase in the affinity of the binding to the target fungal or bacterial cell.

P, P¹ or P² may be formed from the same temperature-responsive monomers or a mixture of different temperature-responsive monomers that polymerise to form the temperature-responsive polymer.

In an embodiment, P, P¹ or P² is branched temperature-responsive polymer formed from the polymerisation of temperature-responsive monomers selected from the group consisting of N-substituted alkyl acrylamides and N-substituted alkyl methacrylamides (such as, for example, N-isopropylacrylamide and N-isopropylmethacrylamide), N,N-di-substituted alkyl acrylamide and N,N-di-substituted alkyl methacrylamides (such as, for example, N,N-isopropylacrylamide and N,N-isopropylmethacrylamide), methyl vinyl ethers, vinyl caprolactam, PEG acrylates, and amino acids (that form temperature-responsive peptides) or mixtures thereof. In a further embodiment, P, P¹ or P² is a branched temperature-responsive polymer formed from the polymerisation of temperature-responsive monomers selected from the group consisting of N-alkyl substituted acrylamides and N-alkyl substituted methacrylamides (such as, for example, N-isopropylacrylamide and N-isopropylmethacrylamide), N,N-di-alkyl substituted acrylamides and N,N-di-alkyl substituted methacrylamides (such as, for example, N,N-isopropylacrylamide and N,N-isopropylmethacrylamide), methyl vinyl ether, vinyl caprolactam, PEG acrylates or mixtures thereof. Suitably, the alkyl groups may comprise 1 to 20 carbons, e.g. 1 to 16 carbons atoms or 1 to 10 carbon atoms.

In a further embodiment, P, P¹ or P² is a branched temperature-responsive polymer formed from the polymerisation of temperature-responsive monomers selected from the group consisting of N-isopropylacrylamide and N-isopropylmethacrylamide, or a mixture thereof. In a further embodiment, P, P¹ or P² is a branched temperature-responsive polymer formed from N-isopropylacrylamide (i.e. the polymer is poly(N-isopropylacrylamide) (PNIPAM)).

In a further embodiment, P, P¹ or P² is selected from branched poly(N-isopropylacrylamide)), branched poly(vinyl methyl ether), branched poly(vinyl caprolactam) or branched poly(poly(ethylene glycol) acrylate).

In a particular embodiment, P, P¹ or P² is branched poly(N-isopropylacrylamide).

In addition to the temperature responsive monomers present in the polymer, a branching agent will also need to be included to provide the required degree of branching in the polymer P, P¹ or P². A branching agent is defined as any compound that can polymerise by addition of radicals to a vinyl functionality and contains also a group that can transfer reversibly during polymerisation in the process known as reversible addition-fragmentation chain transfer (RAFT) polymerisation; such as dithonate (—SC(=S)—; dthiocarbamate (—SC(=S)NH; xanthate (—OC(=S)S—) or trithiocarbonate (—SC(=S)S—). Any suitable branching agent known in the art will suffice. Particular examples of suitable branching agents include: 4-vinylbenzyl-pyrrolecarbodithioate (VPC), vinyl benzyl-phenylcarbodithioate, vinylbenzyl imidazoledithioate, vinylbenzyl alkyldithoates and derivatives thereof. Suitably, the branching agent is selected from 4-vinylbenzyl-pyrrolecarbodithioate (VPC) or vinylbenzyl-phenylcarbodithioate. Most suitably, the branching agent is 4-vinylbenzyl-pyrrolecarbodithioate (VPC).

The molar ratio of temperature responsive monomer to branching agent may be, for example, within a range of 100:1 to 10:1, or 75:1 to 10:1, or 50:1 to 10:1, or 40:1 to 15:1, or 30:1 to 20:1 (e.g. 25:1). The molar percentage of the branching agent in each polymer P, P¹ or P² may be 0.01% to 20%, or 1% to 10%, or 1.5% to 5%, or 2% to 4%.

References to a "branched" polymer P, P¹ or P² herein refer to a temperature-responsive polymer comprising the recited temperature responsive monomers and a proportion of a suitable branching agent as defined above.

In an embodiment, P, P¹ or P² is not a hyperbranched polymer.

In an embodiment, P, P¹ or P² is a branched temperature-responsive polymer having branches occurring at every 3 to 40 monomer units. Suitably, P, P¹ or P² is a branched temperature-responsive polymer having branches occurring at every 3 to 35 monomer units. More suitably, P, P¹ or P² is a branched temperature-responsive polymer having branches occurring at every 10 to 35 monomer units. Even more suitably, P, P¹ or P² is a branched temperature-responsive polymer having branches occurring at every 15 to 35 monomer units. Most suitably, P, P¹ or P² is a branched temperature-responsive polymer having branches occurring at every 15 to 25 monomer units.

In a particular embodiment, P, P¹ or P² is branched poly(N-isopropylacrylamide) and Q is amphotericin B, Q¹ is vancomycin and Q² is polymyxin B.

For the avoidance of doubt, reference made herein to 'Branched-PNIPAM-Amp' indicates a first polymer conjugate in which P is branched poly(N-isopropyl acrylamide) and Q is amphotericin B. Similarly, reference made herein to 'Branched-PNIPAM-Van' indicates a second polymer conjugate in which P¹ is branched poly(N-isopropyl acrylamide) and Q¹ is vancomycin. Similarly, reference made herein to 'Branched-PNIPAM-PMX' indicates a third polymer conjugate in which P² is branched poly(N-isopropyl acrylamide) and Q² is polymyxin B.

In another particular group of first polymer conjugates of the invention, Q is amphotericin B and the first polymer conjugate has the formula IA below:

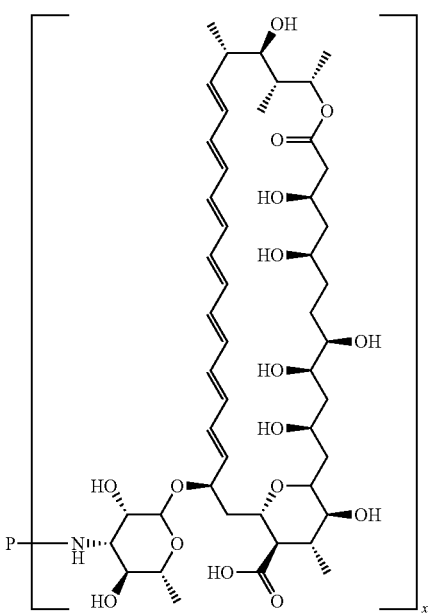

wherein the group in the square brackets is amphotericin B and P and x are each as defined herein before.

In a particular embodiment, the first polymer conjugate has the structural formula IA shown above in which P is branched poly(N-isopropylacrylamide) and each amphotericin B molecule is bound to a terminus of the branched poly(N-isopropylacrylamide) molecule. P further comprises a proportion of a branching agent as defined above.

Methods for forming branched temperature-responsive polymers of the present invention are known in the art. For example, suitable methods for forming branched poly(N-isopropylacrylamide) are described in Rimmer et al.[14] The branched poly(N-isopropylacrylamide) formed by the process described in Rimmer et al.[14] possesses functional carboxy groups at the termini of the polymer branches, which can be reacted with amine groups present on suitable Q groups (e.g. amphotericin B), $Q^1$ groups (e.g. vancomycin) or $Q^2$ groups (e.g. polymyxin B) to form amide linkages attaching one or more Q, $Q^1$ or $Q^2$ groups to one or more termini of the branched poly(N-isopropylacrylamide).

Chemical methodologies for forming other linkages between P, $P^1$ or $P^2$ with Q, $Q^1$ or $Q^2$ respectively are well known in the art.

The polymer conjugates defined herein may be present in any suitable amount in the hydrogel compositions of the present invention. Suitably, the first, second and/or third polymer conjugates are independently present in the hydrogel compositions of the present invention in an amount of the between 0.5 and 50 wt %. More suitably, the first, second and/or third polymer conjugates are independently present in the hydrogel compositions of the present invention in an amount of the between 0.5 and 30 wt %. Even more suitably, the first, second and/or third polymer conjugates are independently present in the hydrogel compositions of the present invention in an amount of the between 0.5 and 20 wt %. Most suitably, the first, second and/or third polymer conjugates are independently present in the hydrogel compositions of the present invention in an amount of the between 5 and 20 wt %.

In a particular embodiment, the first polymer conjugate is present in the hydrogel compositions of the present invention in an amount of the between 15 and 30 wt %, the second polymer conjugate is present in the hydrogel compositions of the present invention in an amount of the between 10 and 25 wt %, and the third polymer conjugate is present in the hydrogel compositions of the present invention in an amount of the between 20 and 50 wt %.

The first, second and/or third polymer conjugate may be attached to the hydrogel polymeric matrix using synthetic techniques well-known in the art. The first, second and/or third polymer conjugates are typically prepared with a percentage of their (terminal) functional groups covalently attached to each Q, $Q^1$ and $Q^2$ ligand respectively. Unreacted, or free, (terminal) functional groups on the branched temperature-responsive polymers, P, $P^1$ and $P^2$, of each respective the polymer conjugate may then be reacted with functional groups on the hydrogel polymer matrix to form a covalent attachment there between. Suitably, the functional groups present on the hydrogel polymer matrix are amino groups and the (terminal) functional groups on the branched temperature-responsive polymers, P, $P^1$ and $P^2$, of each respective the polymer conjugate are ester groups (i.e. N-hydroxysuccinimide activated esters).

Thus, in a further aspect, the present invention provides a hydrogel composition comprising a hydrogel polymer matrix, an aqueous medium (e.g. water) and the polymer conjugates as defined herein. Suitably, the polymer conjugates of the invention are independently covalently attached to the hydrogel polymer matrix. More suitably, the polymer conjugates of the invention are independently covalently attached to the hydrogel polymer matrix, by the reaction of (terminal) functional groups present on the branched temperature-responsive polymers, P, $P^1$ and $P^2$, of each respective polymer conjugate with functional groups present on the hydrogel polymer matrix, to form one of the following linking groups:

—$NR_1$—, —O—, —C(O)—O—, —O—C(O)—, C(O)—$NR_1$, —$NR_1$—C(O)—, —N($R_1$)C(O)O—, —O(O)CN($R_1$)—, —S—, —S(O)—, —S(O)$_2$—, —S(O)$_2$—$NR^1$, —$NR^1$—S(O)$_2$— or a triazole linking group (formed by "click" chemistry), wherein $R_1$ is hydrogen or (1-4C)alkyl (e.g. methyl).

In a particular embodiment, the polymer conjugates of the invention are independently covalently attached to the hydrogel polymer matrix, by the reaction of (terminal) carboxyl or ester groups present on the branched temperature-responsive polymers, P, $P^1$ and $P^2$, of each respective polymer conjugate with amine groups present on the hydrogel polymer matrix, to form —C(O)—NH— linking groups.

Suitably, the ester groups present on the branched temperature-responsive polymers, P, $P^1$ and $P^2$, of the polymer conjugates are succinimide esters groups (e.g. N-hydroxysuccinimide (NHS) or N-hydroxysulfosuccinimide (Sulfo-NHS) activated esters).

In an embodiment, between 1% and 30% of the total (terminal) functional groups of each branched temperature-responsive polymers, P, $P^1$ and/or $P^2$, are covalently attached to the hydrogel polymer matrix. Suitably, between 1% and 20% of the total (terminal) functional groups of each branched temperature-responsive polymer, P, $P^1$ and/or $P^2$, are covalently attached to the hydrogel polymer matrix. More suitably, between 1% and 15% of the total (terminal) functional groups of each branched temperature-responsive polymer, P, $P^1$ and/or $P^2$, are covalently attached to the hydrogel polymer matrix. Even more suitably, between 1% and 10% of the total (terminal) functional groups of each branched temperature-responsive polymer, P, $P^1$ and/or $P^2$, are covalently attached to the hydrogel polymer matrix.

Most suitably, between 1% and 5% of the total (terminal) functional groups of each branched temperature-responsive polymer, P, $P^1$ and/or $P^2$, are covalently attached to the hydrogel polymer matrix.

It will be appreciated that the hydrogel polymer matrix may be any suitable polymer matrix that is capable of forming a hydrogel upon exposure to water. Suitable polymer matrixes are well-known in the art and may be ready selected by a person skilled in the art. Non-limiting examples of suitable hydrogel polymer matrixes include polyacrylate based polymer matrixes, polyethylene glycol based polymer matrixes, polyvinylalcohol based matrixes, polyvinylpyrrolidone based polymer matrixes, polyacrylamide based polymer matrixes and combinations thereof. Suitably, the hydrogel polymer matrix is charge neutral.

In an embodiment, the hydrogel polymer matrix is a polyacrylate based polymer matrix.

In another embodiment, the hydrogel polymer matrix is a polyacrylate based polymer matrix formed from the reaction between glycerol monomethacrylate (GMMA), glycidyl methacrylate (GME) and ethylene glycol dimethacrylate (EGDMA).

In an embodiment, the water content of the hydrogel is greater than 50% w/w and more suitably it is greater than 70% w/w, 80% w/w or 90% w/w.

Particular Embodiments

The following numbered paragraphs relate to particular embodiments of the present invention:
1.1 a hydrogel composition comprising a hydrogel polymeric matrix and a first polymer conjugate, or a salt thereof, having the general formula:

$P-[Q]_x$ wherein:
P is a branched poly(N-isopropylacrylamide), a branched poly(vinyl methyl ether), a branched poly(vinyl caprolactam) or a branched poly(poly(ethylene glycol) acrylate, and wherein each of which comprises:
a) a plurality of terminal carboxyl and/or terminal ester groups, wherein one or more of said terminal carboxyl and/or terminal ester groups are covalently attached to Q; and
b) a proportion of branching agents as defined above;
Q is amphotericin B, nystatin or natamycin; and
x is the percentage of terminal carboxyl groups on the branched temperature-responsive polymer, P, that are attached to Q, wherein x is greater than or equal to 50%;
together with:
i) a second polymer conjugate, or a salt thereof, having the general formula:

$P^1-[Q^1]_y$ wherein:
$P^1$ is a branched poly(N-isopropylacrylamide), a branched poly(vinyl methyl ether), a branched poly(vinyl caprolactam) or a branched poly(poly(ethylene glycol) acrylate, wherein each of which comprises:
a) a plurality of terminal carboxyl and/or terminal ester groups, wherein one or more of said terminal carboxyl and/or terminal ester groups are covalently attached to $Q^1$; and
b) a proportion of branching agents as defined above;

$Q^1$ is a ligand capable of binding to Gram positive bacteria; and
y is the percentage of functional groups on the branched temperature-responsive polymer, $P^1$, that are attached to $Q^1$, wherein y is greater than or equal to 50%;
and/or
ii) a third polymer conjugate, or a salt thereof, having the general formula:

$P^2-[Q^2]_z$ wherein:
$P^2$ is a branched poly(N-isopropylacrylamide), a branched poly(vinyl methyl ether), a branched poly(vinyl caprolactam) or a branched poly(poly(ethylene glycol) acrylate, wherein each of which comprises:
a) a plurality of terminal carboxyl and/or terminal ester groups, wherein one or more of said terminal carboxyl and/or terminal ester groups are covalently attached to $Q^2$; and
b) a proportion of branching agents as defined above;
$Q^2$ is a ligand capable of binding to Gram negative bacteria; and
z is the percentage of functional groups on the branched temperature-responsive polymer, $P^2$, that are attached to $Q^2$, wherein z is greater than or equal to 50%.
1.2 a hydrogel composition comprising a hydrogel polymeric matrix and a first polymer conjugate, or a salt thereof, having the general formula:

$P-[Q]_x$ wherein:
P is a branched poly(N-isopropylacrylamide), a branched poly(vinyl methyl ether), a branched poly(vinyl caprolactam) or a branched poly(poly(ethylene glycol) acrylate, wherein each of which comprises:
a) a plurality of terminal carboxyl and/or terminal ester groups, wherein one or more of said terminal carboxyl and/or terminal ester groups are covalently attached to Q; and
b) a proportion of branching agents as defined above;
Q is amphotericin B; and
x is the percentage of terminal carboxyl groups on the branched temperature-responsive polymer, P, that are attached to Q, wherein x is greater than or equal to 70%;
together with:
i) a second polymer conjugate, or a salt thereof, having the general formula:

$P^1-[Q^1]_y$ wherein:
$P^1$ is a branched poly(N-isopropylacrylamide), a branched poly(vinyl methyl ether), a branched poly(vinyl caprolactam) or a branched poly(poly(ethylene glycol) acrylate, wherein each of which comprises:
a) a plurality of terminal carboxyl and/or terminal ester groups, wherein one or more of said terminal carboxyl and/or terminal ester groups are covalently attached to $Q^1$; and
b) a proportion of branching agents as defined above;
$Q^1$ is vancomycin; and y is the percentage of functional groups on the branched temperature-responsive polymer, $P^1$, that are attached to $Q^1$, wherein y is greater than or equal to 70%;
and/or
ii) a third polymer conjugate, or a salt thereof, having the general formula:

$P^2\text{-}[Q^2]_z$ wherein:
  $P^2$ is a branched poly(N-isopropylacrylamide), a branched poly(vinyl methyl ether), a branched poly(vinyl caprolactam) or a branched poly(poly(ethylene glycol) acrylate, wherein each of which comprises:
    a) a plurality of terminal carboxyl and/or terminal ester groups, wherein one or more of said terminal carboxyl and/or terminal ester groups are covalently attached to $Q^2$; and
    b) a proportion of branching agents as defined above;
  $Q^2$ is polymyxin B; and
  z is the percentage of functional groups on the branched temperature-responsive polymer, $P^2$, that are attached to $Q^2$, wherein z is greater than or equal to 70%.

1.3 a hydrogel composition comprising a hydrogel polymeric matrix and a first polymer conjugate, or a salt thereof, having the general formula:

$P\text{-}[Q]_x$ wherein:
  P a branched poly(N-isopropylacrylamide) comprising:
    a) a plurality of terminal carboxyl and/or terminal ester groups, wherein one or more of said terminal carboxyl and/or terminal ester groups are covalently attached to Q; and
    b) between 0.01 and 20 mole percent of a 4-vinylbenzyl-pyrrolecarbodithioate (VPC) branching agent;
  Q is amphotericin B; and
  x is the percentage of terminal carboxyl groups on the branched temperature-responsive polymer, P, that are attached to Q, wherein x is greater than or equal to 80%;
together with:
i) a second polymer conjugate, or a salt thereof, having the general formula:

$P^1\text{-}[Q^1]_y$ wherein:
  $P^1$ a branched poly(N-isopropylacrylamide) comprising:
    a) a plurality of terminal carboxyl and/or terminal ester groups, wherein one or more of said terminal carboxyl and/or terminal ester groups are covalently attached to Q; and
    b) between 0.01 and 20 mole percent of a 4-vinylbenzyl-pyrrolecarbodithioate (VPC) branching agent;
  $Q^1$ is vancomycin; and
  y is the percentage of functional groups on the branched temperature-responsive polymer, $P^1$, that are attached to $Q^1$, wherein y is greater than or equal to 80%;
and/or
ii) a third polymer conjugate, or a salt thereof, having the general formula:

$P^2\text{-}[Q^2]_z$ wherein:
  $P^2$ is a branched poly(N-isopropylacrylamide) comprising:
    a) a plurality of terminal carboxyl and/or terminal ester groups, wherein one or more of said terminal carboxyl and/or terminal ester groups are covalently attached to Q; and
    b) between 0.01 and 20 mole percent of a 4-vinylbenzyl-pyrrolecarbodithioate (VPC) branching agent;
  $Q^2$ is polymyxin B; and
  z is the percentage of functional groups on the branched temperature-responsive polymer, $P^2$, that are attached to $Q^2$, wherein z is greater than or equal to 80%.

1.4 a hydrogel composition comprising a hydrogel polymeric matrix, and a first polymer conjugate, or a salt thereof, having the general formula:

$P\text{-}[Q]_x$ wherein:
  P a branched poly(N-isopropylacrylamide) comprising:
    a) a plurality of terminal carboxyl and/or terminal ester groups, wherein one or more of said terminal carboxyl and/or terminal ester groups are covalently attached to Q; and
    b) between 0.01 and 20 mole percent of a 4-vinylbenzyl-pyrrolecarbodithioate (VPC) branching agent;
  Q is amphotericin B; and
  x is the percentage of terminal carboxyl groups on the branched temperature-responsive polymer, P, that are attached to Q, wherein x is greater than or equal to 80%;
together with:
i) a second polymer conjugate, or a salt thereof, having the general formula:

$P^1\text{-}[Q^1]_y$ wherein:
  $P^1$ a branched poly(N-isopropylacrylamide) comprising:
    a) a plurality of terminal carboxyl and/or terminal ester groups, wherein one or more of said terminal carboxyl and/or terminal ester groups are covalently attached to Q; and
    b) between 0.01 and 20 mole percent of a 4-vinylbenzyl-pyrrolecarbodithioate (VPC) branching agent;
  $Q^1$ is vancomycin; and
  y is the percentage of functional groups on the branched temperature-responsive polymer, $P^1$, that are attached to $Q^1$, wherein y is greater than or equal to 80%;
and/or
ii) a third polymer conjugate, or a salt thereof, having the general formula:

$P^2\text{-}[Q^2]_z$ wherein:
P² is a branched poly(N-isopropylacrylamide) comprising:
  a) a plurality of terminal carboxyl and/or terminal ester groups, wherein one or more of said terminal carboxyl and/or terminal ester groups are covalently attached to Q; and
  b) between 0.01 and 20 mole percent of a 4-vinylbenzyl-pyrrolecarbodithioate (VPC) branching agent;
Q² is polymyxin B; and
z is the percentage of functional groups on the branched temperature-responsive polymer, P², that are attached to Q², wherein z is greater than or equal to 80%;
and wherein:
1) said hydrogel polymeric matrix is a polyacrylate based polymer matrix; and
2) the polymer conjugates are independently covalently attached to the hydrogel polymer matrix by the reaction of terminal carboxyl or ester groups present on the branched temperature-responsive polymers, P, P¹ and P², of each respective polymer conjugate with amine groups present on the hydrogel polymer matrix, to form —C(O)—NH— linking groups.

Applications of the Hydrogel Compositions of the Invention

A principal application of the hydrogel compositions of the present invention relates to their utility for binding to fungi and Gram positive and/or Gram negative bacterial cells present in a sample, thereby enabling the presence of fungi and/or bacterial cells in the sample to be detected. To facilitate this, the hydrogel composition is incubated with the sample (e.g. a sample obtained from a human or animal patient, or directly contacted with a site of the human or animal body (e.g. a cornea)) for a period of time and then removed and analysed for any fungal cells and Gram positive and/or Gram negative bacterial cells that have bound to the polymer conjugates present in the hydrogel.

The hydrogel can be physically removed from the sample and the presence of any fungal and/or bacterial cells bound to the polymer conjugates can be determined by a variety of conventional techniques, including selective staining and imaging techniques well known in the art.

In an embodiment, the hydrogel matrix is in the form of a membrane, contact lens, swab or wound dressing.

The ability of the polymer conjugates of the present invention to bind to fungal and/or bacterial cells also makes them suitable materials for physically removing fungal and/or bacterial cells from a sample (e.g. an infected wound, a mucosal surface or another sample obtained from the environment). For example, if the polymer conjugates for the present invention are bound to a hydrogel membrane, contact lens, swab or wound dressing, they can be used to physically bind to fungal and/or bacterial cells that then come into contact with and physically remove them from an infected site.

The present invention also provides a method of detecting the presence of fungal cells, Gram positive bacterial cells and/or Gram negative bacterial cells in a sample, the method comprising:
  (i) contacting a hydrogel composition, contact lens, membrane, swab or wound dressing as defined herein with the sample;
  (ii) removing either the hydrogel composition, contact lens, membrane, swab or wound dressing as defined herein from the sample and testing the hydrogel composition, contact lens, membrane, swab or wound dressing for the presence of bound fungal cells, Gram positive bacterial cells and/or Gram negative bacterial cells.

In yet another aspect, the present invention provides a method of determining the presence of a fungal infection, a Gram positive bacterial infection and/or a Gram negative bacterial infection, the method comprising:
  (i) contacting a hydrogel composition, contact lens, membrane, swab or wound dressing as defined herein with either a sample obtained from the suspected site of infection or with the suspected site of infection directly; and
  (ii) removing the hydrogel composition, contact lens, membrane, swab or wound dressing and determining whether any fungal cells, Gram positive bacterial cells and/or Gram negative bacterial cells are bound to the hydrogel composition, contact lens, membrane, swab or wound dressing respectively.

In yet another aspect, the present invention provides a method of diagnosing the presence of a fungal infection, a Gram positive bacterial infection and/or a Gram negative bacterial infection, the method comprising:
  (i) contacting a polymer conjugate, composition, hydrogel composition, contact lens, membrane, swab or wound dressing as defined herein with either a sample obtained from the suspected site of infection or with the suspected site of infection directly;
  (ii) removing the conjugate, composition, hydrogel composition, contact lens, membrane, swab or wound dressing from the sample;
  (iii) determining whether any fungi are attached to the conjugate, composition, hydrogel composition, contact lens, membrane, swab or wound dressing; and
  (iv) and optionally determining the type of fungi, Gram positive bacteria and/or Gram negative bacteria detected.

The present invention also provides the use of a hydrogel composition, contact lens, membrane, swab or wound dressing as defined herein for detecting the presence of fungi in a biological sample or diagnosing a fungal infection.

In order to determine whether any fungi are bound to a conjugate, composition, hydrogel composition, contact lens, membrane, swab or wound dressing of the present invention, the material can be analysed under a microscope, subjected to staining techniques and then viewed under a microscope or using other techniques such as labelled ligands (e.g. antibodies) to bind to any bound fungal cell present and be detected.

In a particular embodiment, selective fluorescent staining techniques are used to identify any fungi, Gram positive bacteria and/or Gram negative bacteria that are bound to the hydrogel composition, contact lens, membrane, swab or wound dressing of the present invention. Such techniques are known in the art.

EXAMPLES

Examples of the invention will now be described, for the purpose of illustration only, with reference to the accompanying figures, in which:

FIG. 1 shows—Electrospray mass spectra of Amp-B: A) example of negative ion spectrum (black); B) example of positive ion spectrum (grey); Calibration curve for Amp B using electrospray mass spectrometry.

FIG. 2 shows—a) UV Spectra of Amphotericin B in Methanol with varying concentrations, b) GPC chromatogram UV detector response at 405 nm of Amp B at various concentrations. c) calibration curve (at 405 nm) derived from stand alone UV/visible spectrometry and d) from GPC chromatogram (at 405 nm); (e) GPC chromatograms of Branched-PNIPAM-Amp (UV absorbance at 405 nm) and signal from refractive index detector. Also shown is the chromatogram of Amp-B alone (UV response).

Figure 5:
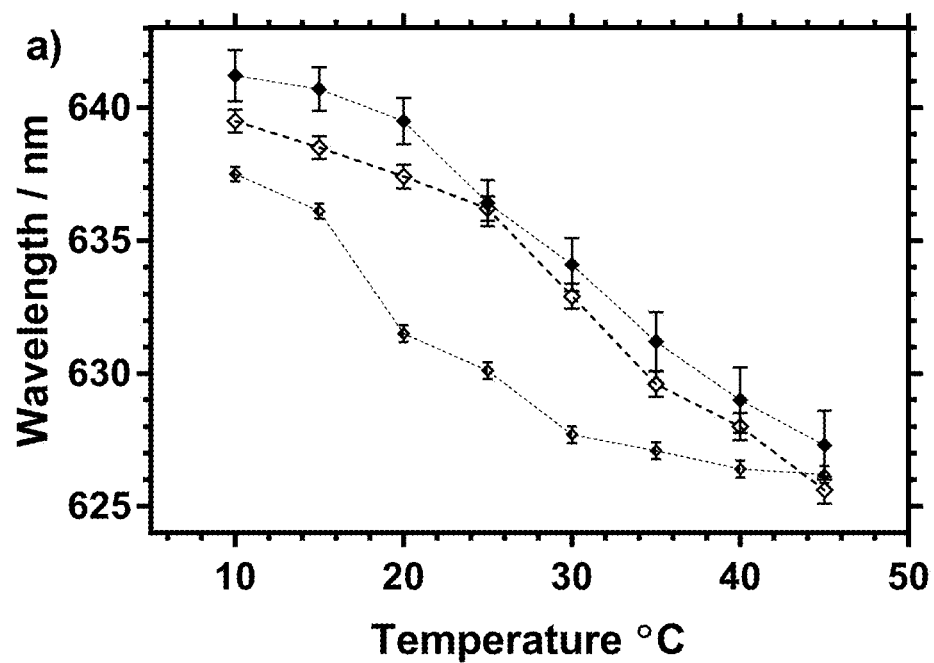
Figure 5:
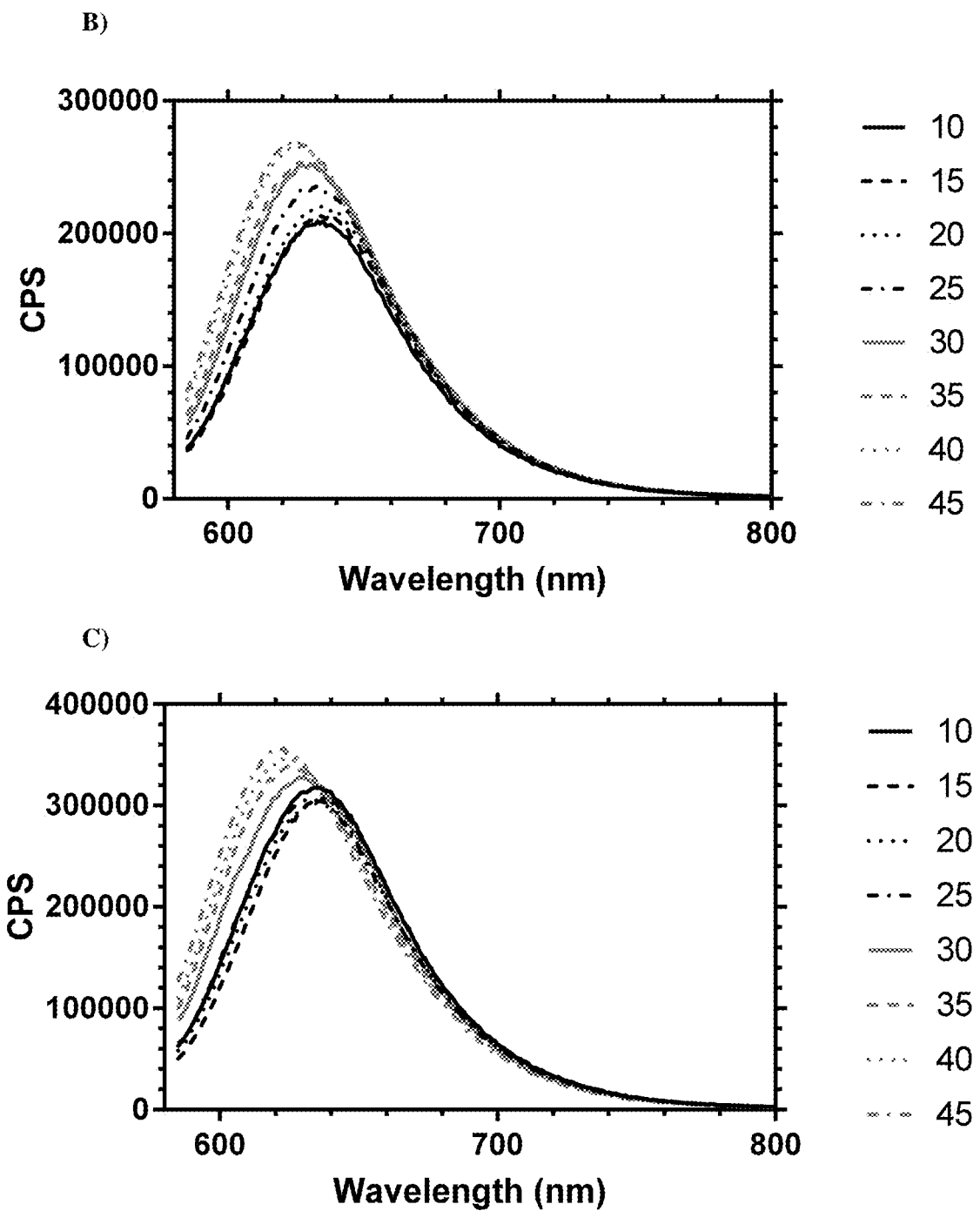

FIG. 5 shows A) the peak fluorescence emission wavelength of the spectra of nile red in solutions of Branched-PNIPAM-Amp (1 mg/ml) alone (◆); mixed with 1:1 ergosterol (◇) across $T_{CRIT}$ and the wavelength of the peak emission in the presence of Branched-PNIPAM-Py (■); B,C) Fluorescence emission spectra of nile red in solutions of Branched-PNIPAM-Amp for B) Branched-PNIPAM alone, and C) Branched-PNIPAM-Amp in the presence of ergosterol. Spectra obtained following excitation at 580 nm.

Figure 6:
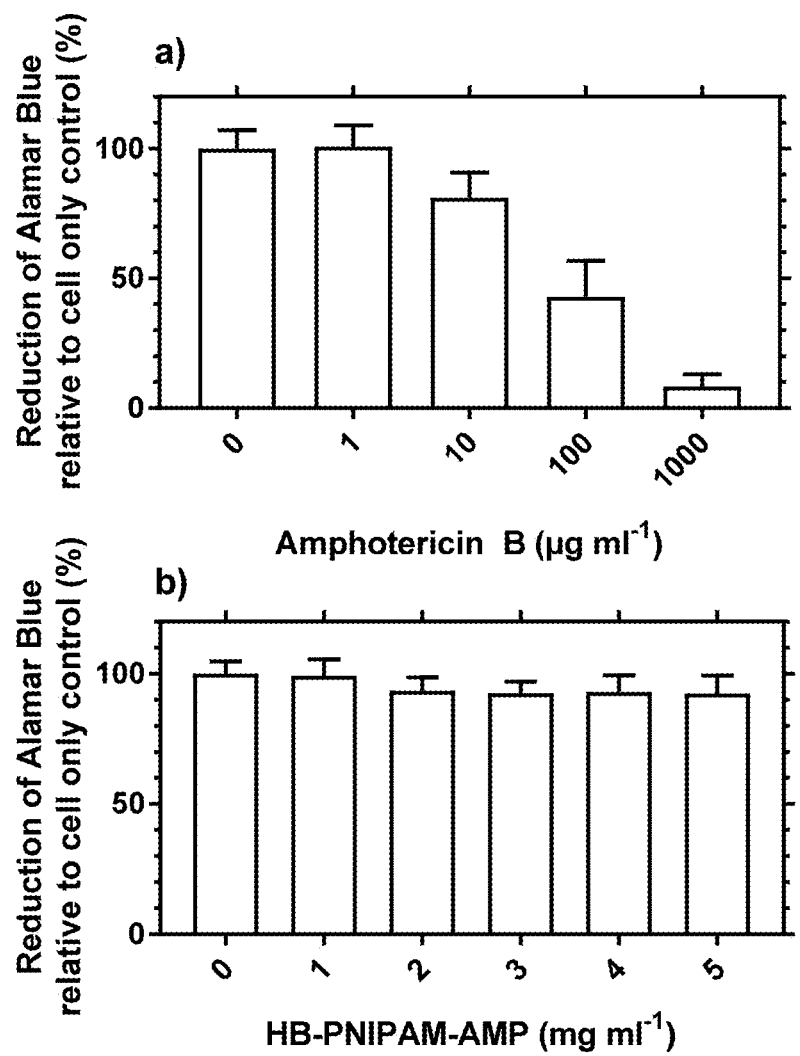

FIG. 6 Viability of rabbit corneal epithelial cells in the presence of increasing concentrations of A. Amp-B or B. branched-PNIPAM-Amp. The data show the significantly higher susceptibility of the cells to low concentrations of Amp-B and the lower toxicity of the polymer variant.

Figure 7:
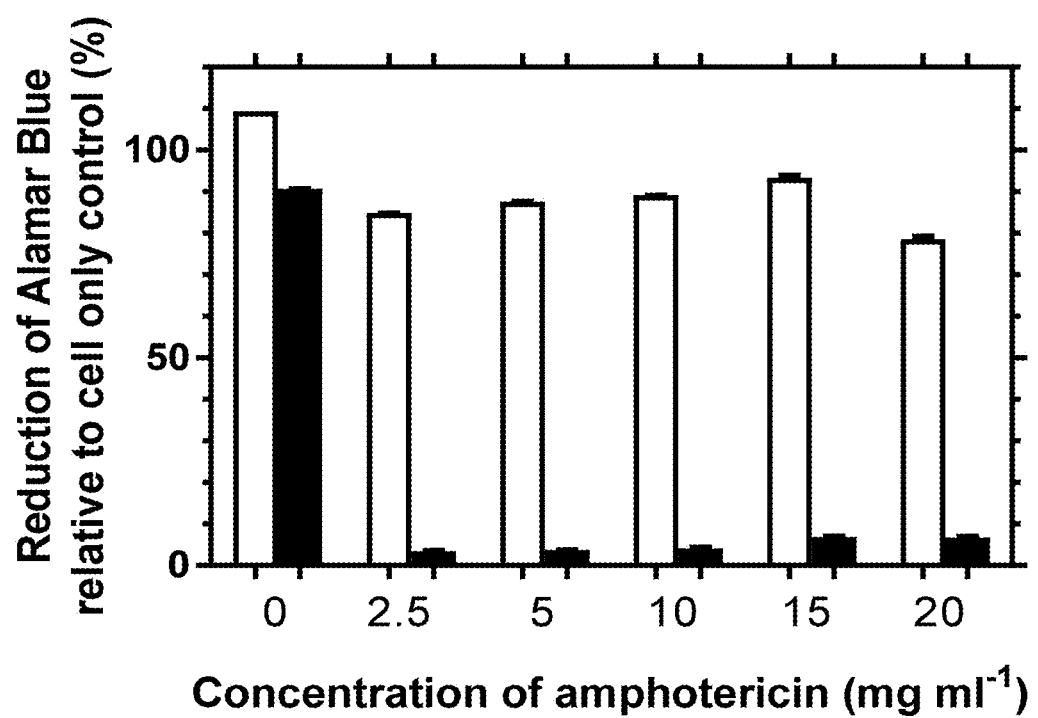

FIG. 7 shows the human corneal biocompatibility of Branched-PNIPAM-Amp (white) and free amphotericin (black).

Figure 8:
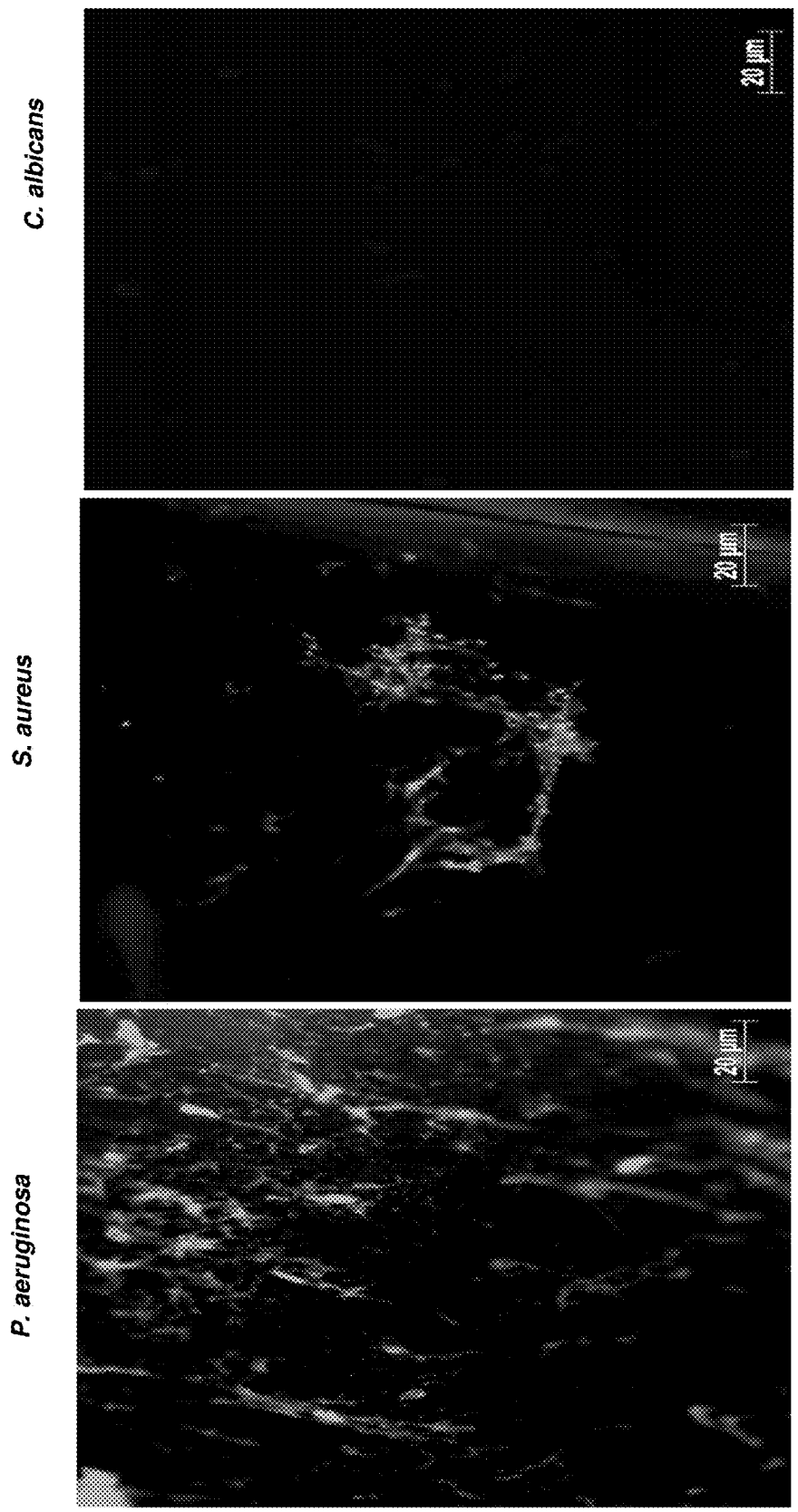

FIG. 8 shows Staphylococcus. aureus, Pseudomonas aeruginosa, Candida albicans bound to a Triple hydrogel (example 2).

Figure 9:
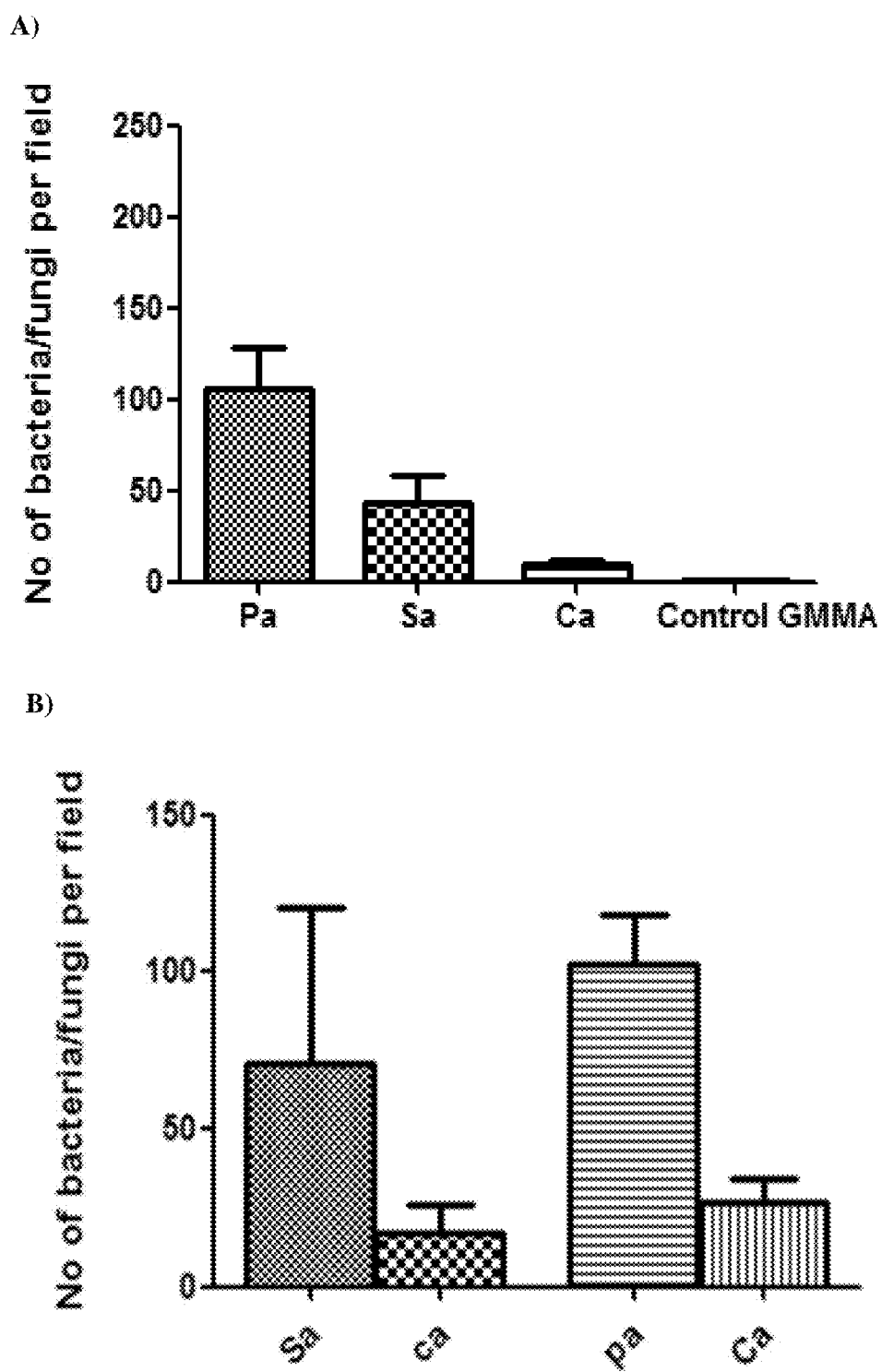
Figure 10A:
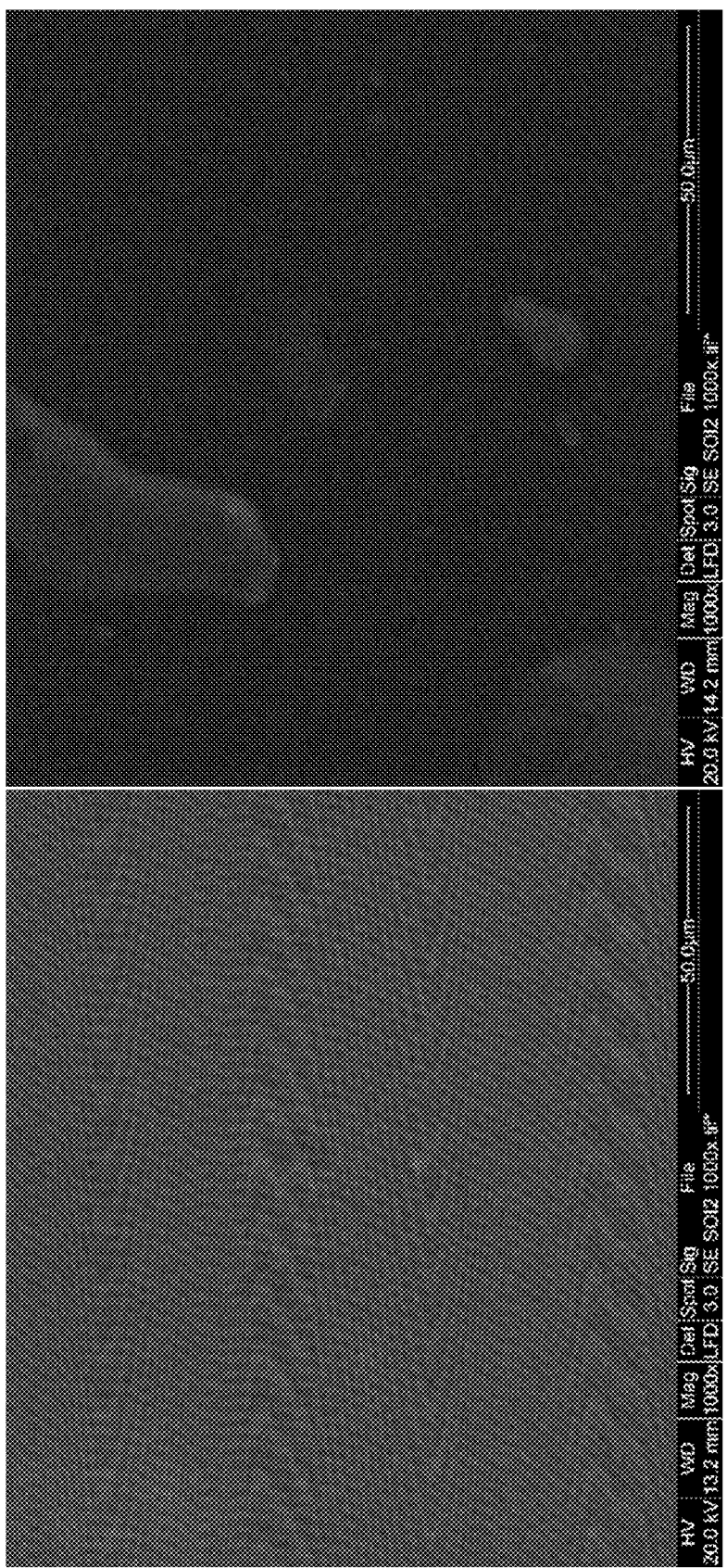
Figure 10B:
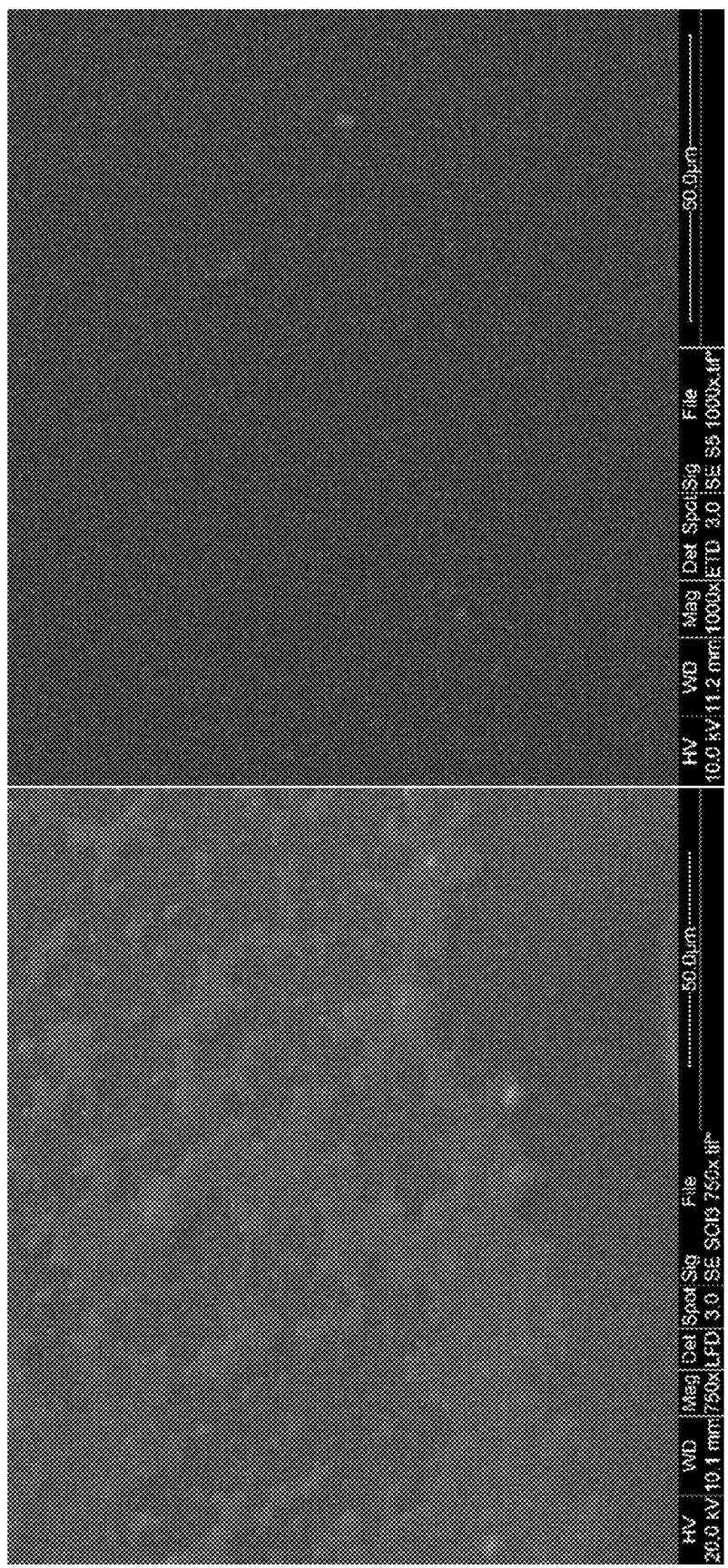
Figure 10C:
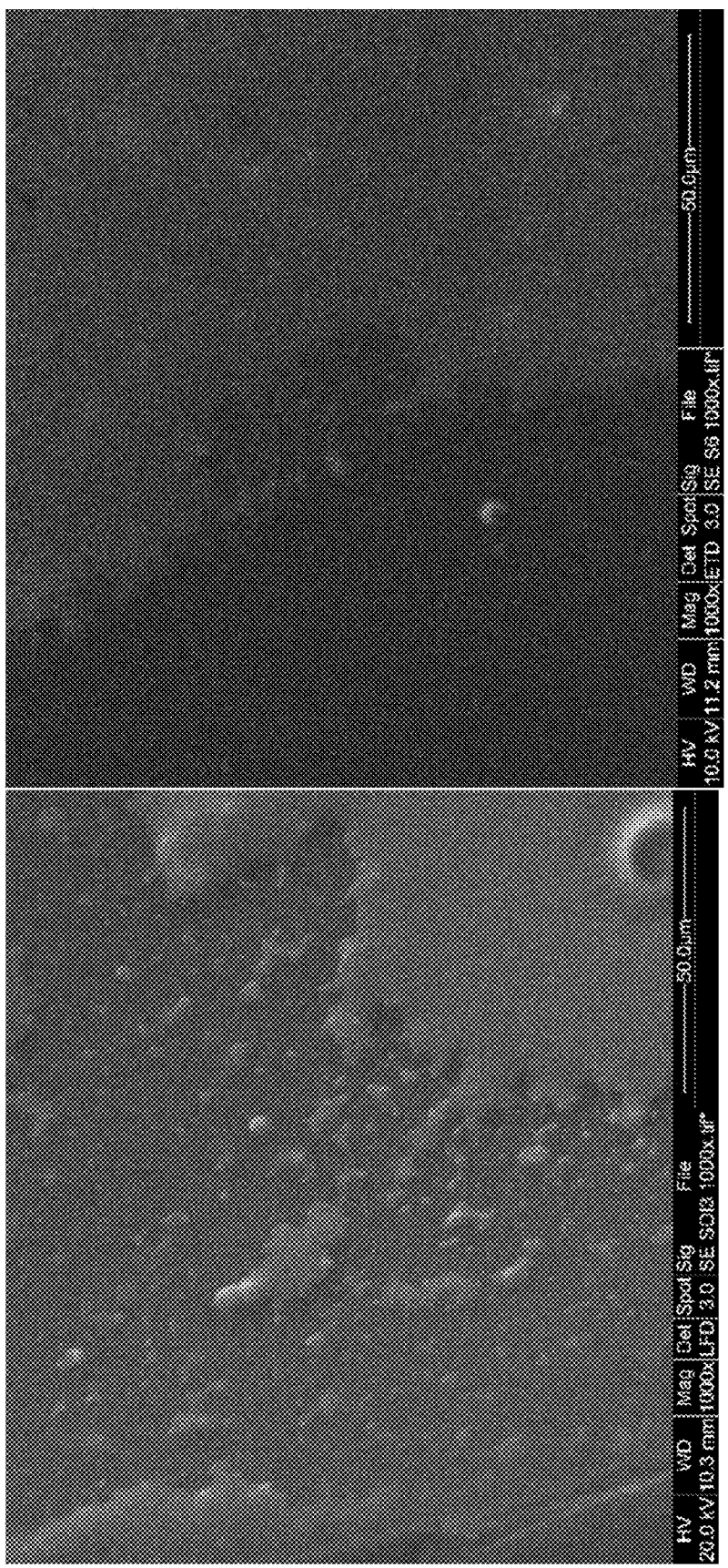

FIG. 9 Shows bacteria/fungi bound to a Triple functionalised (HB-PNIPAM-Van, HB-PNIPAM-PMX and HB-PNIPAM-Amp) hydrogel in infected rabbits (A) data from infection with the single species indicated; (B) data from duel species infected rabbits (see Example 2). Hydrogels were kept over infected eyes for 30 min then washed, stained and imaged. Data 8A and 8B shows the mean number of cells per field of view±SD. Sa=Staphylococcus aureus, Pa=Pseudomonas aeruginosa, Ca=Candida albicans FIG. 10 Shows SEM images of S. aureus and P. aeruginosa bound to hydrogels. $10^8$ cfu S. aureus and P. aeruginosa suspensions were exposed to A) non-functionalised, B) Single HB-PNIPAM-Van and C) Triple functional hydrogel sheets. SEM imaging of the sheets show the formation of soft bacterial films only for the corresponding gram-positive bacteria; S. aureus on HB-PNIPAM-Van functional hydrogels and P. aeruginosa only on the Triple functional hydrogel.

Figure 11:
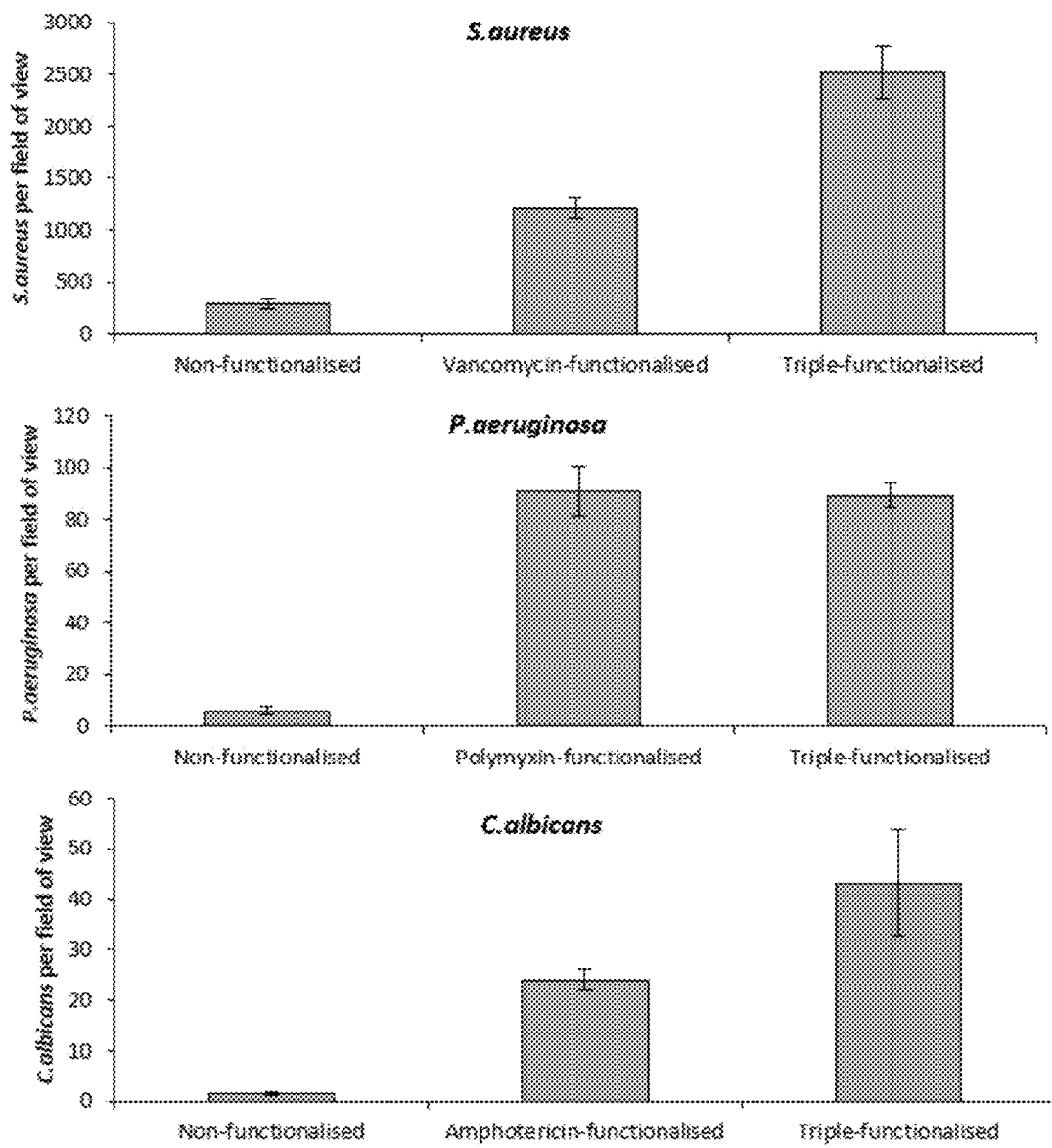

FIG. 11 shows the mean number of bacterial or fungal cells that bound to the surface of single functionalised hydrogels and to the triple functionalised hydrogel compared to a non-funtionalised control hydrogel. As can be seen, each functionalised hydrogel bound significantly more organisms than the non-functionalised control hydrogel (p<0.0001). More S. aureus bound than P. aeruginosa or C. albicans.

Figure 12:
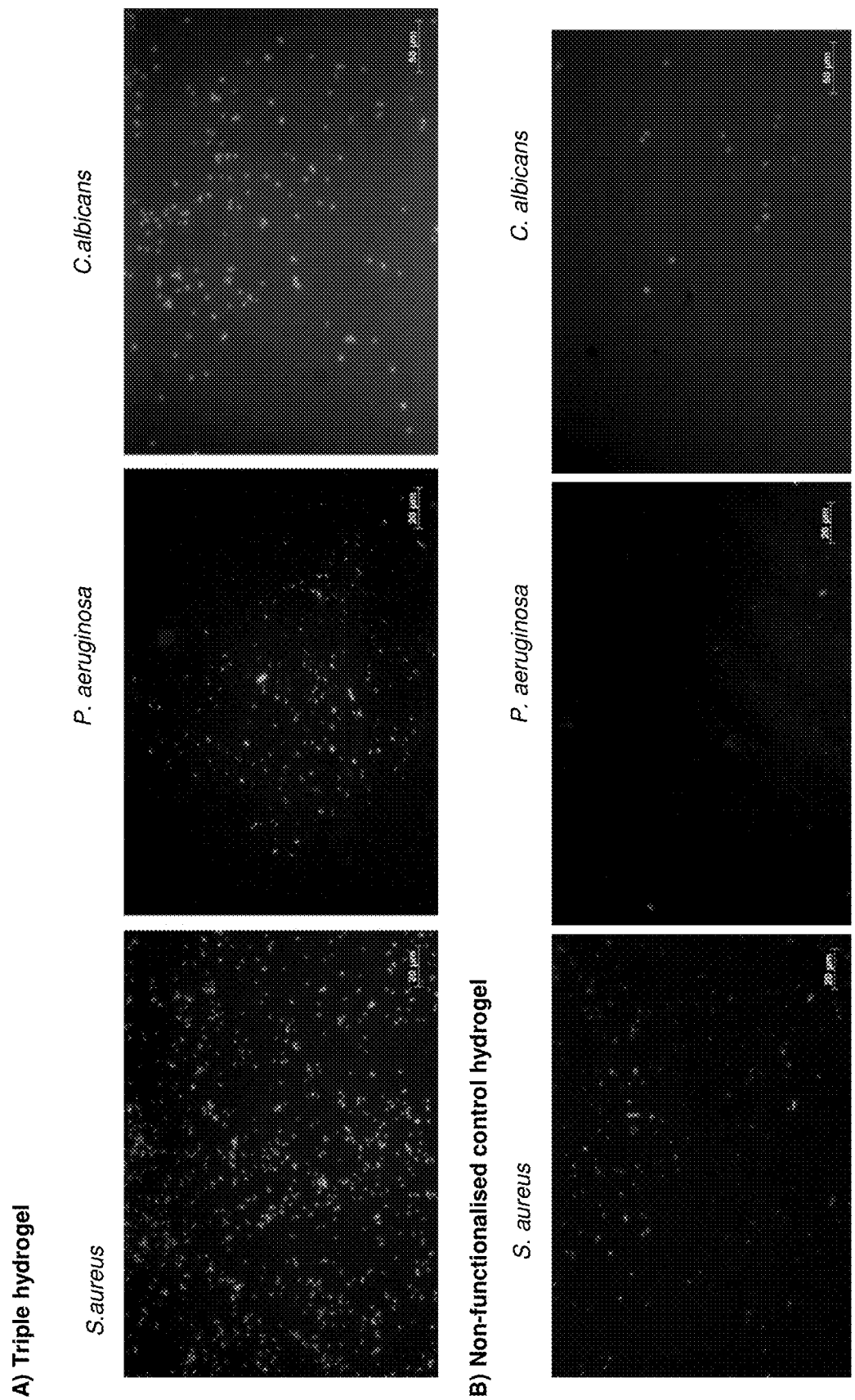

FIG. 12 shows optical micrographs of bacteria and fungi bound to hydrogel surfaces compared to a non-functionalised control hydrogel.

Figure 13:
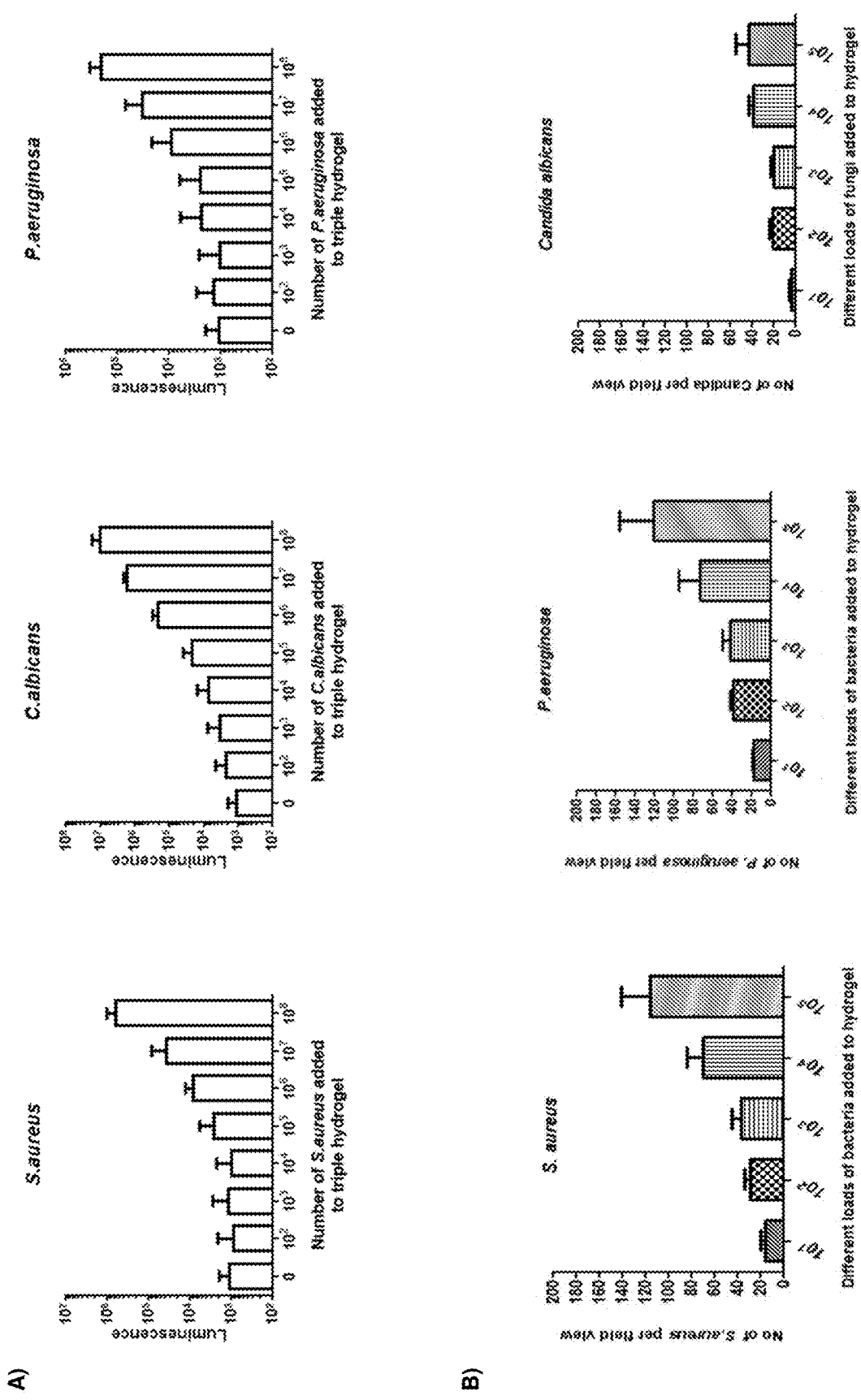

FIG. 13 shows the quantification of organisms A) using luminescence derived from an assay of ATP) and B) from counting the number of organisms in view in a microscope. Data used to determine the limit of detection of the triple hydrogel. Increasing numbers of each organism were incubated in vitro with triple (vancomycin, polymyxin and amphotericin polymer) functionalised hydrogels for 1 hour. Hydrogels were washed and then either A) the ATP assay was applied or B) they were examined with a fluorescence microscope and the number of organisms per field of view counted. Data are mean±SD of 8 fields of view per hydrogel from at least 3 independent experiments.

Figure 14:
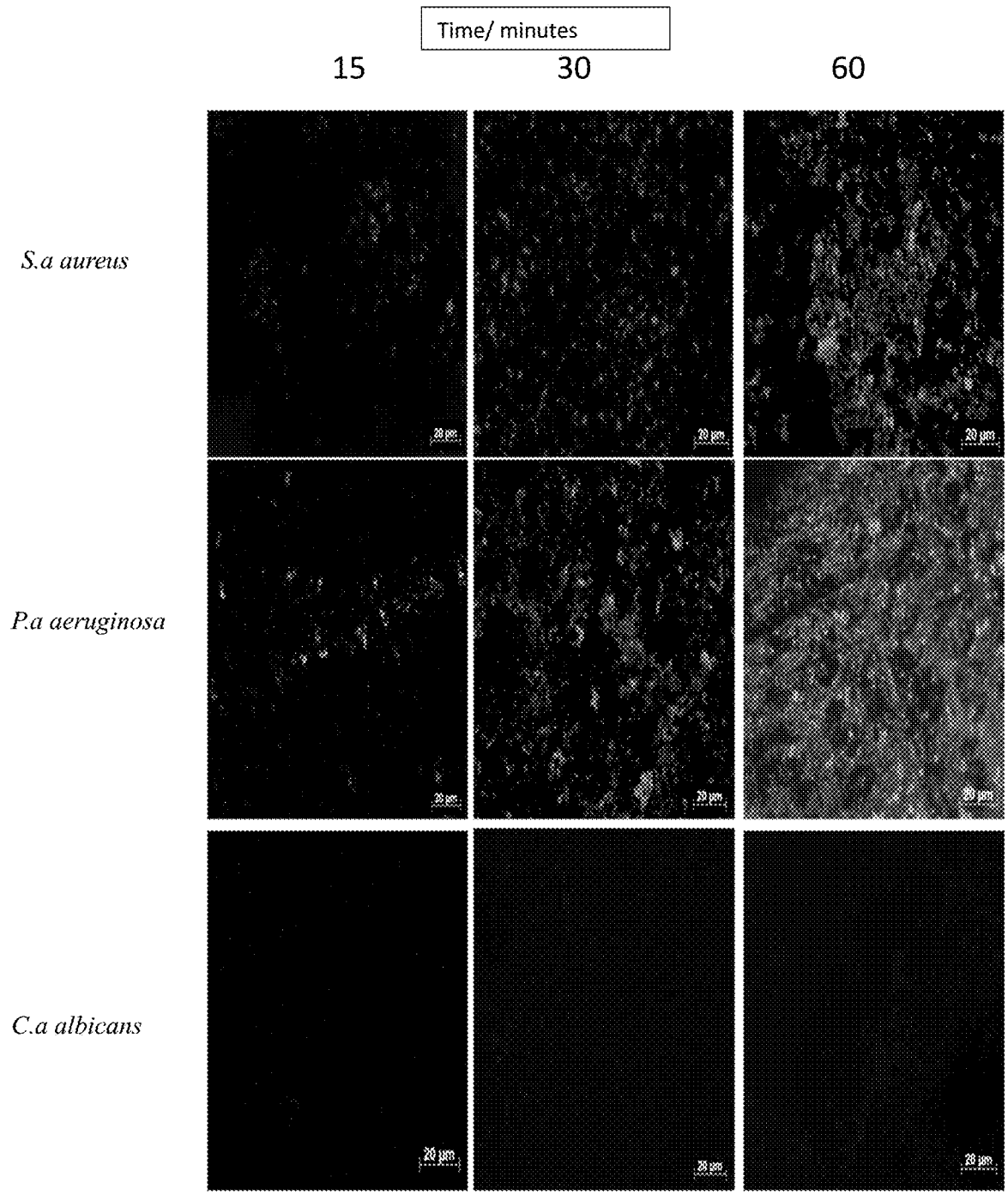

FIG. 14 shows S. aureus (S), P. aeruginosa (P), and C. albicans (C) cells adhering to the surface of the triple hydrogel at different time points.

Figure 15:
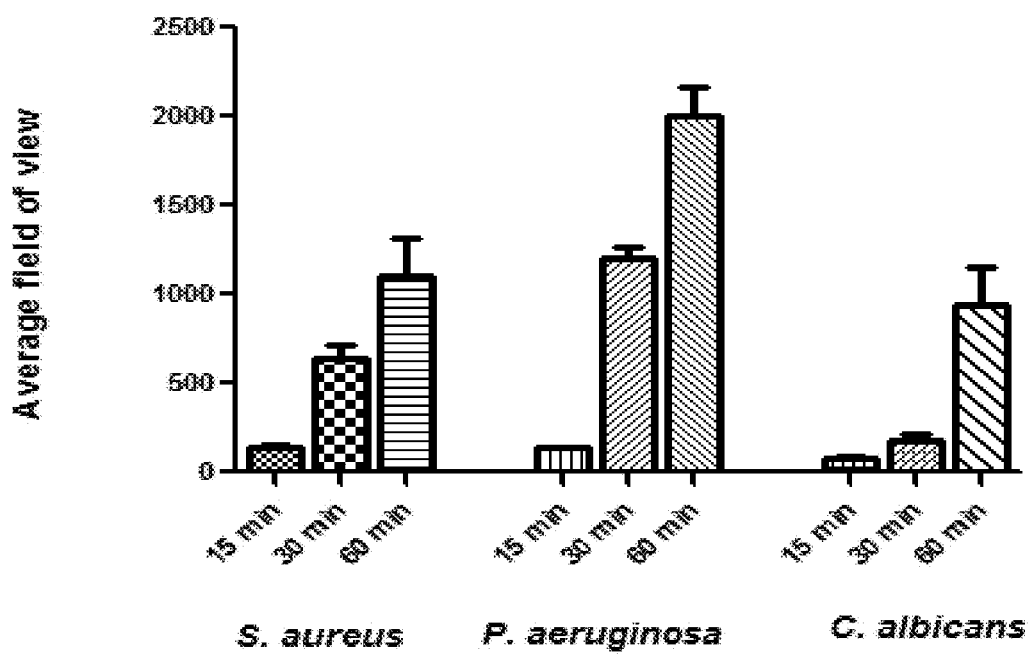

FIG. 15 shows S. aureus, P. aeruginosa, C. albicans and F. solani infections detected using a triple functionalised hydrogel.

Figure 16:
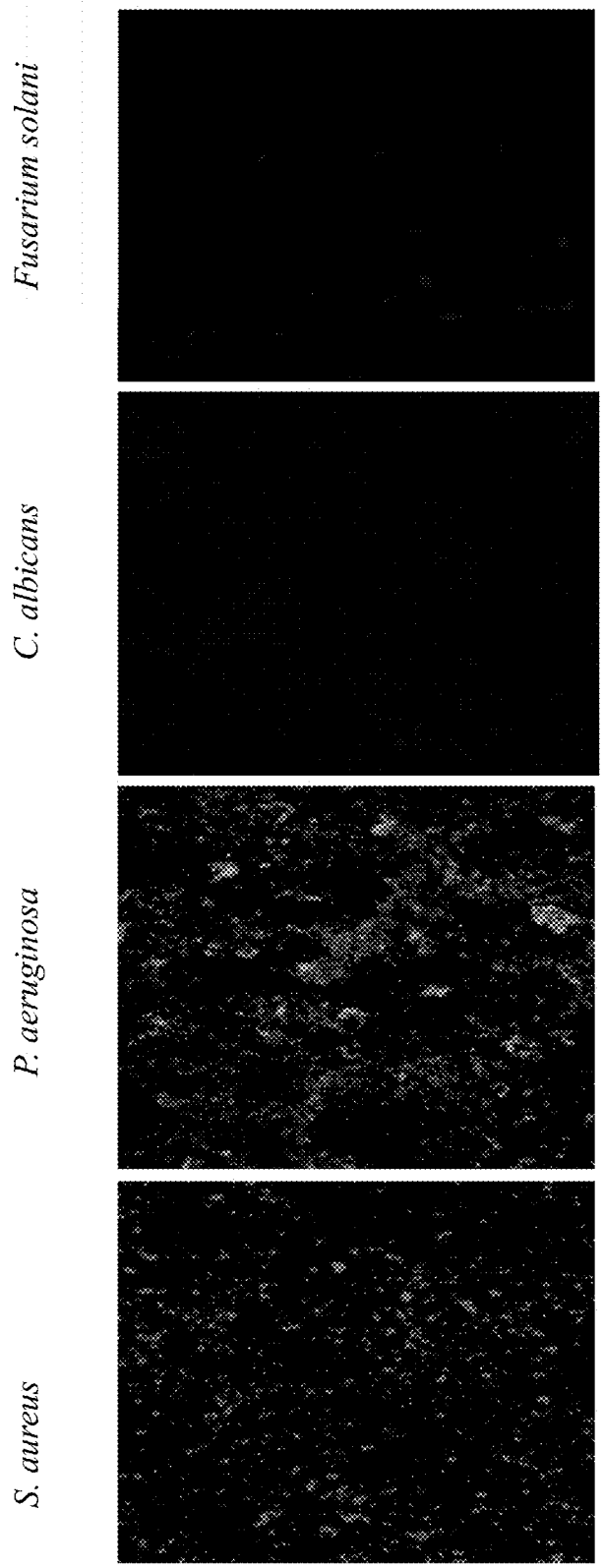
Figure 17:
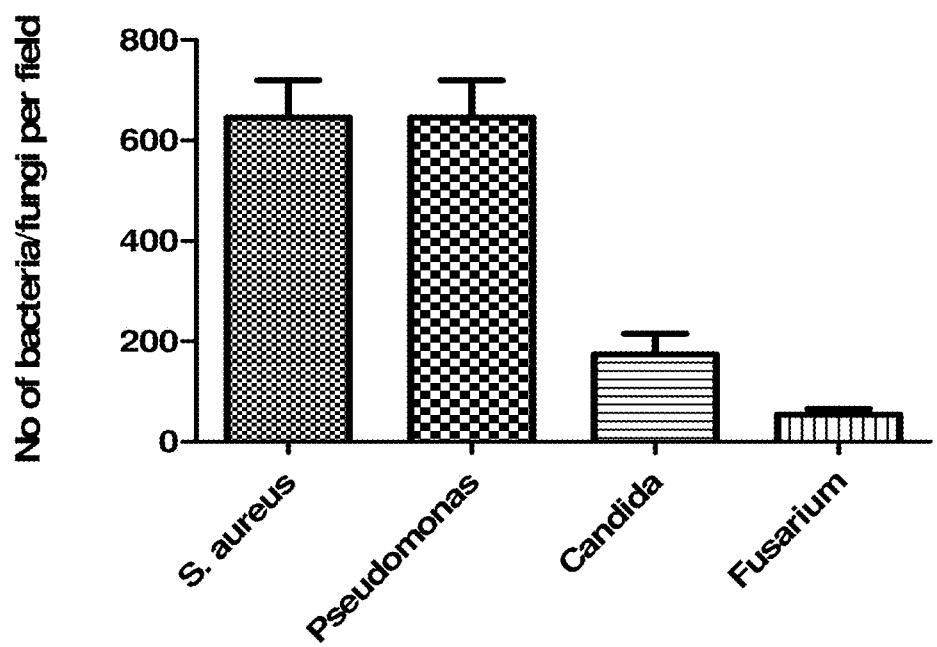

FIG. 16 shows representative images (A) of triple functionalised hydrogels removed from infected human corneas and stained and the number of organisms recovered in culture from hydrogels FIG. 17 shows S. aureus, P. aeruginosa, C. albicans and F. solani infections detected using a triple functionalised hydrogel.

Figure 18:
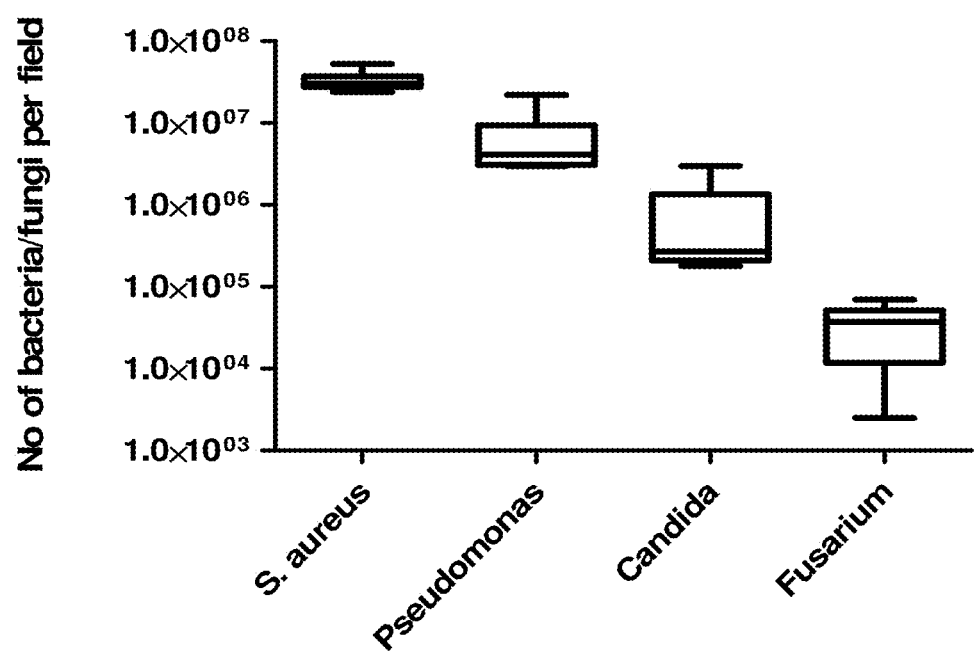

FIG. 18 shows the number of organisms (CFU) recovered from infected ex-vivo human corneas. S. aureus, P. aeruginosa, C. albicans or F. Solani.

Figure 19:
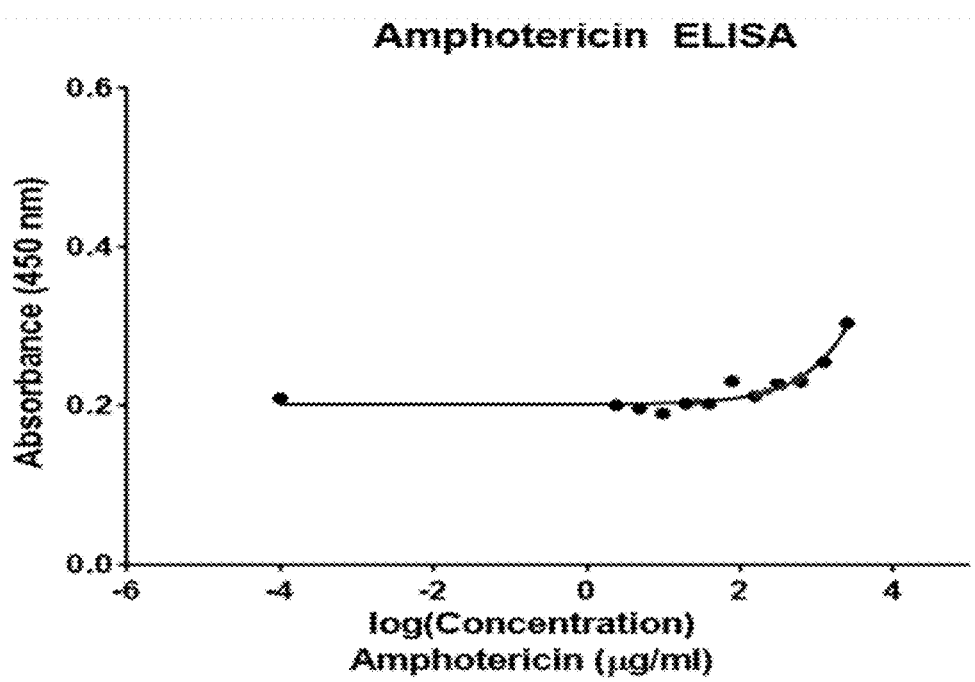

FIG. 19 shows the ELISA measurements of hydrogel discs to determine Amp-B content, where multiple samples (n=9) were analysed.

Figure 20:
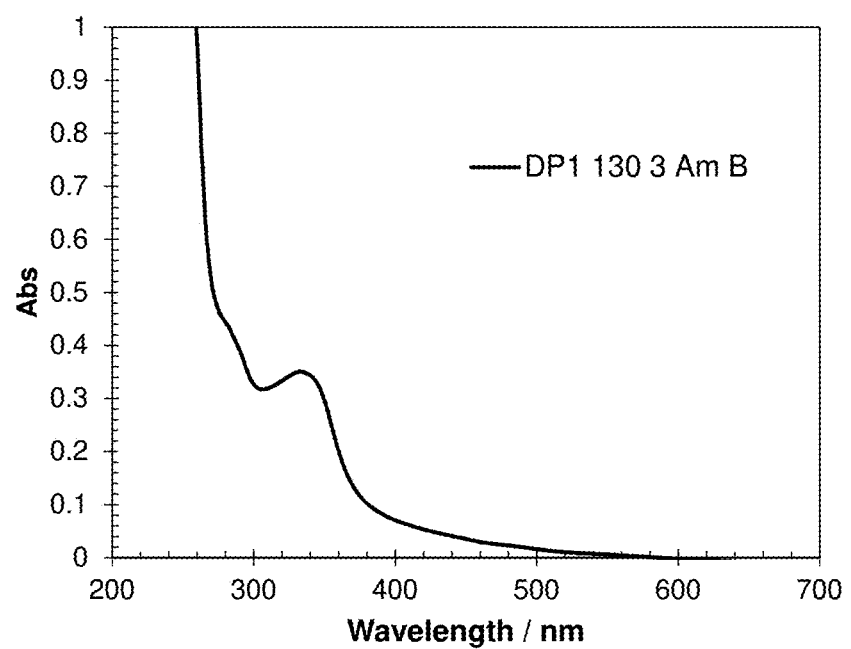

FIG. 20 shows the UV absorption data with increased ΔUV Absorption of amphotericin hydrogels over the base material.

Figure 21:
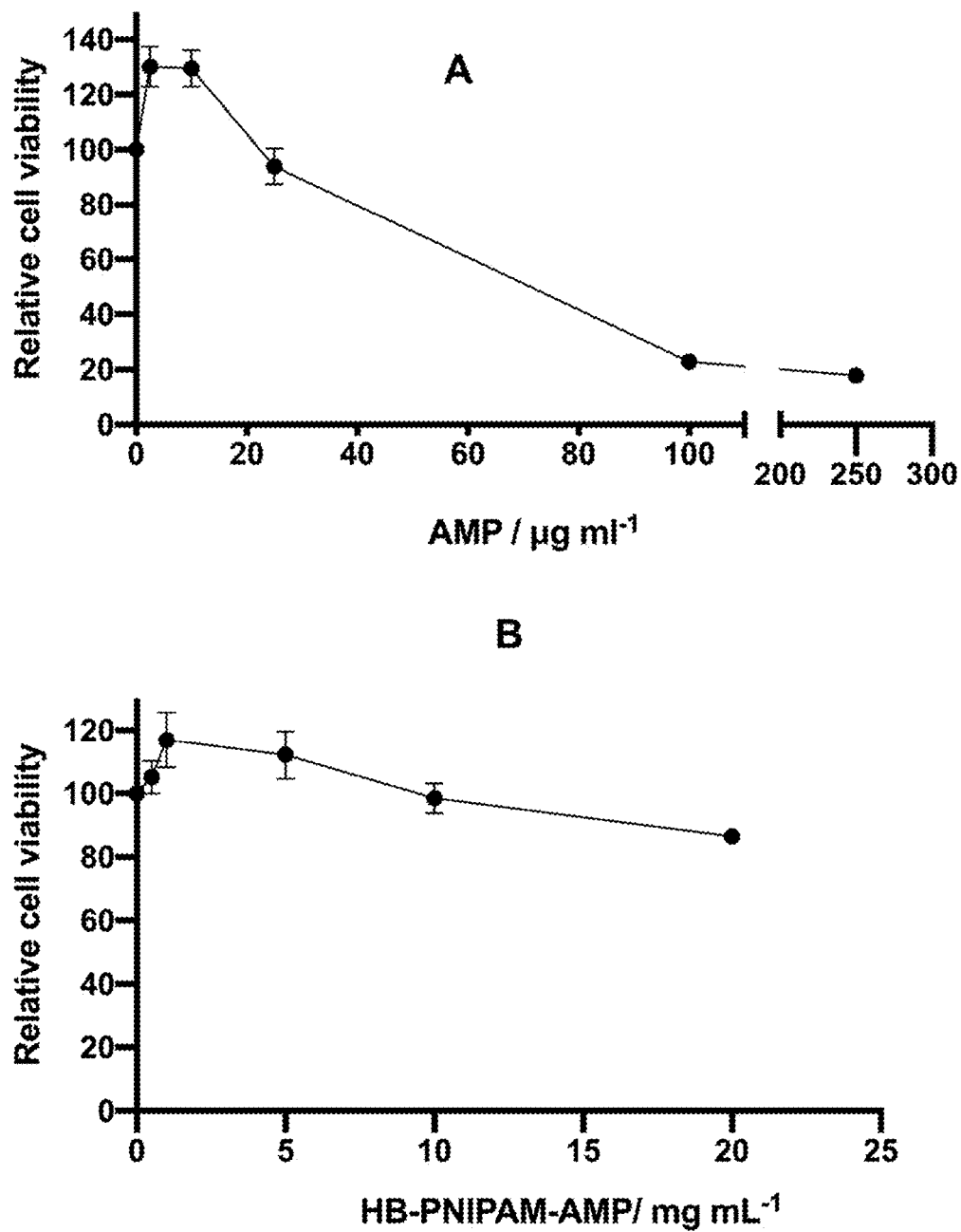

FIG. 21 shows cell viability relative to controls (in the absence of Branched-PNIPAM-Amp or Amp-B) for A) Amp-B; and B) Branched-PNIPAM-Amp, with human renal epithelial cells.

EXAMPLE 1—SYNTHESIS AND CHARACTERISATION OF PNIPAM-AMPHOTERICIN B CONJUGATES

Materials and Methods

All materials were used as supplied unless otherwise stated. Stated material purities were N-isopropyl acrylamide (NIPAM) (Aldrich, 97%), N-hydroxy succinimide (Aldrich, 98%), dicyclohexyl carbodiimide (Aldrich, 98%), Amphotericin B (Cambridge Bioscience, >95%), dichloromethane (HPLC grade), Nile Red (Sigma, 99%) and ethyl acetate (HPLC grade) were supplied by Sigma Aldrich. N-isopropyl acrylamide was recrystallised from hexane/toluene. 4,4'-Azobis(4-cyanovaleric acid) (ACVA) (98% purity) was obtained from Alfa Aeser and dried in vacuo at room temperature overnight. Branching chain transfer agent (CTA) 4-Vinylbenzyl-pyrrole-carbodithioate (1) was synthesised and purified according to a previously reported method[15]. Dioxane (Analar grade), diethyl ether (anhydrous), dimethyl formamide (Analar grade), ethanol (Analar grade), acetone (Analar grade) and hydrochloric acid (35% wt/wt) were obtained from VWR, Ltd. Cell culture reagents were purchased from Sigma-Aldrich unless otherwise stated. Dispase II was purchased from Roche and epidermal growth factor was purchased from Invitrogen. Mouse 3T3 fibroblasts were obtained from ATCC, Manassas, Va. and an established cell line-J2 3T3 cells originally obtained from Professor Howard Green, USA. Wild brown rabbit heads were kindly provided by the BlackFace Meat Company in Dumfries, Scotland. Human corneas were obtained from Ramayamma International Eye Bank, LV Prasad Eye Institute, Hyderabad. Due to the low solubility of Amphotericin B[16], for biological assays, Amphotericin B BioReagent (Sigma-Aldrich) was used.

Synthesis of Branched-PNIPAM Precursor

Acid ended polymer was prepared via dissolution of 1 (3.667 g, 14.1 mmol), ACVA (3.96 g, 14. 1 mmol) and NIPAM (40.00 g, 353.5 mmol) in 1,4-dioxane (280 ml) to a sealed round bottom flask. This was bubbled with nitrogen for thirty minutes to degas the solvent before heating (60° C., 48 hours) under a nitrogen atmosphere. The reaction mixture was precipitated into diethyl ether and the precipitate collected and dried in vacuo overnight. The solid was weighed and characterised by $^1$H NMR [400 MHz, DMSO (ppm): 1.02 (6H, s, —N(CH$_3$)$_2$) 1.40 (2H, br m, CH$_2$—CH—Ar—) 1.95 (2H, br m, —CH$_2$—CH—CO—NH—), 3.82 (H$_2$O-polymer), 6.41 (H$_2$, br s, N-pyrrole-H), 7.13 (br m, —Ar—), 7.7 (2H br s, N-pyrrole-H)], Sulphur content (1.81%), LCST (19.0° C.) and DOSY (298 K peak $R_{Hn}$=2.33, $R_{Hw}$=2.40). The term "HB-PNIPAM" is used synonymously herein with "Branched-PNIPAM".

Synthesis of Branched-PNIPAM-Amp

The highly-branched polymer was then re-dissolved in 400 ml dimethyl formamide with additional ACVA (73.22 g, 259.2 mmol), nitrogen was bubbled through the solution which was then heated and stirred for 18 hours under nitrogen. Additional ACVA was added to the mixture (73.22 g, 259.2 mmol) which was reacted for an additional 18 hours before a final addition of ACVA (73.22 g, 259.2 mmol) and further reacted for another final 18 hours. The reaction mixture was precipitated into diethyl ether then reprecipitated from acetone into diethyl ether. The final product was dissolved in acetone with 10% ethanol and ultrafiltered three times to remove the low molar mass component, then the solvent was removed by rotary evaporation. A solid yield of 95% was characterised by $^1$H NMR ($^1$H NMR [400 MHz, DMSO (ppm): 1.02 (6H, s, —N(CH$_3$)$_2$) 1.43 (2H, br m, CH$_2$—CH—Ar—) 1.98 (2H, br m, —CH$_2$—CH—CO—NH—), 3.79 (H$_2$O-polymer), 7.17 (br m, —Ar—)], Sulphur content (0.25%), LCST (22.2° C.). The polymer was stored at −18° C. The acid ended polymer (5.00 g) was dissolved in DMF (55 ml). To this, a solution of N-Hydroxysuccinimide (0.858 g, 7.46 mmol) and N—N-Dicyclohexylcarbodiimide (DCC) (1.539 g, 7.46 mmol) in DMF (15 ml) was added. The mixture was stirred under N$_2$ overnight and all solid products removed via gravity filtration. The remaining solution was precipitated into diethyl ether, dissolved in ethanol and concentrated via ultrafiltration three times. The remaining solvent was removed by rotary-evaporation and the solid dried under vacuum at room temperature. This succinimide precursor polymer (1.00 g) was dissolved in ice-cold water (50 ml). A solution of Amphotericin-B (30 mg, 0.032 moles) in 0.1 M sodium phosphate buffer (pH 8.5, 10 ml) and water (10 ml) was added to the polymer solution (1.0 g). Via addition of 0.01 M NaOH solution the pH was increased to pH 11 while stirring on ice overnight, then at RT for 24 hours. The solution was ultrafiltered in water using 10 kDa pore membrane filters in water at pH 11 (250 ml extracted—repeated seven times), then once again at pH 7 (250 ml extraction) before the sample was freeze-dried. The final product was a pale yellow solid (0.99 g yield) and was characterised by $^1$H NMR [400 MHz, DMSO (ppm): 1.05 (6H, s, —N(CH$_3$)$_2$) 1.55 (2H, br m, CH$_2$—CH—Ar—) 2.01 (2H, br m, —CH$_2$—CH—CO—NH—), 3.82 (H$_2$O-polymer), 7.26 (br m, —Ar—)], sulfur content (0.24%), LOST (36.0° C.) and DOSY ($R_{Hn}$=2.55 nm, $R_{Hw}$=2.66 nm) and stored at −18° C.

Instrumentation

Polymer characterisation was carried out by nuclear magnetic resonance (NMR) spectroscopy of solutions in DMSO-D$_6$. Measurements were obtained with a Bruker Avance spectrometer operating at 400 MHz ($^1$H) and 100 MHZ ($^{13}$C). The sulphur content was determined by elemental analysis via combustion as % of total sample by weight. LOST measurements were carried out on a Nano DSC by TA Instruments; polymer samples were dissolved in H$_2$O at 5 mg ml$^{-1}$ and stored at 5° C. for 24 hours prior to use to ensure complete dissolution. Samples were run over the temperature range 3-75° C. with a heating rate of 1.5° C. per minute and cooling rate of 1° C. per minute. The Tc-g was taken as the temperature at the thermogram peak maximum. Electrospray mass spectra of the polymer were recorded using a Micromass Quattro LC from Kinesis Solutions. Amphotericin solutions were prepared in methanol (spectroscopic grade) ranging in concentration from 10 μg ml$^{-1}$ to 0.103 μg ml$^{-1}$, and additional spike solutions mixed with 0.98 mg ml$^{-1}$ NIPAM were run from 0.49-4.9 μg ml$^{-1}$ to ensure the presence of polymer did not reduce detection efficiency. Samples were injected directly into the device via a syringe pump at a rate of 10 μl min$^{-1}$.

UV absorbance measurements were carried out both in-line on the GPC instrumentation and in 1 cm path length cuvettes using a Varian Cary 50 probe UV-Visible spectrometer.

Polymer molar mass distribution was recorded via gel permeation chromatography (GPC) on a methanol based system as we described previously. Samples were dissolved in methanol (1 mg ml$^{-1}$) and injected through two Agilent Polargel-M columns (high molar mass range) with a flow rate of 1 ml minute[17]. They were analysed via comparison to a universal calibration using linear PNIPAM standards via triple RI, UV and viscometric detection to give absolute molar mass averages ($M_N$, $M_W$ $M_Z$ and two forms of dispersity (Đ) $M_w/M_n$ and $M_z/M_w$).

The polymer hydrodynamic radius was calculated via DOSY NMR spectroscopy to calculate diffusion (D), which was converted to hydrodynamic radius using the Stokes Einstein as shown in equation 1. Sample internal viscosity (η) was found using sample solvent shift as outlined previously[17].

$$D = \frac{k}{6\pi} \qquad \text{Eq. 1}$$

Fluorescence Dye Studies of Polymer Solutions

A stock solution of nile red was made up by adding 2 mg of nile red to 5 cm$^3$ DMSO. This was diluted (to 10$^{-7}$ mol dm$^{-3}$) with ultrapure water. Branched-PNIPAM polymers (11 mg) were dissolved in ultrapure water (7 ml) and nile red stock solution (100 μl) was added. The fluorescence spectrum was then recorded on a Horiba Fluoromax-4 excitation 580 nm, emission 560-800 nm, with slit widths of 1 nm. Peak wavelength emission and intensity was calculated from the Gaussian distribution of wavelengths following previously published protocols.[15]

Culture Conditions for *C. albicans*

*C. albicans* cells, laboratory strain SC5314 or ATCC90028, were cultured on solid BHI (Oxoid) medium at 37° C. for 24 hours and stored at 4° C. for up to one month. Prior to experiments, a colony of *C. albicans* was subcultured into liquid BHI medium overnight at 37° C.

Isolation and Culture of Rabbit Limbal Epithelial Cells

Limbal rims from corneal-scleral buttons were excised from wild brown rabbit heads, as previously described.[18] Tissue was immersed in 2.5 mg ml$^{-1}$ (w/v) dispase II solution in DMEM for 1 hour at 37° C. The limbal rims were subsequently scraped gently using forceps to remove the epithelial cells. The dispase-cell suspension was centrifuged at 200 g for 5 minutes and re-suspended in culture medium containing DMEM: Ham's F12 (1:1) supplemented with 10% foetal calf serum, 100 U ml$^{-1}$ penicillin and 100 U ml$^{-1}$ streptomycin, 2.5 μg ml$^{-1}$ amphotericin B, 5 μg ml$^{-1}$ insulin and 10 ng ml$^{-1}$ epidermal growth factor. Cells were cultured with irradiated 3T3-mouse fibroblasts at a cell density of 2.4×10$^4$ cells cm$^{-2}$ in culture medium. Cells were not used beyond passage 3. For experiments, cells were seeded into 24 well-plates at 5×10$^4$ cells per well and cultured for 24 hours.

Rabbit Limbal Epithelial Cell Viability

Prior to determining the viability of rabbit limbal epithelial cells, cells were washed 3× with phosphate-buffered saline (PBS, 0.01M, pH 7.4) to remove residual antimicrobials. Branched-PNIPAM-Amp (20, 15, 10, 5, 4, 3, 2, 2.5, 1 and 0 mg ml$^{-1}$) or Amphotericin B (0, 1, 10, 100, 1000 μg ml$^{-1}$ or 0, 2.5, 5, 10, 15, 20 mg ml$^{-1}$) were dissolved in culture medium without penicillin, streptomycin or Amphotericin B, and added to pre-seeded epithelial cells or human donor corneas (halved) for a further 24 hours. Epithelial cell/cornea viability was determined using Alamar Blue reagent (5 μg ml$^{-1}$) dissolved in PBS. Cells/corneas were incubated with Alamar Blue for 30 minutes and the fluorescence of the solution determined at 570 nm excitation and 585 nm emission (Infinite 200, Tecan). Data for each polymer is presented as percentage viability relative to an untreated control. Each assay was performed in triplicate and data represents the mean±SD from three independent experiments. The decrease in cellular viability after exposure to Branched-PNIPAM-Amp or amphotericin B compared with a cell only control was determined using a Student's t test for single comparisons or ANOVA for multiple comparisons.

Human Renal Epithelial Cell Viability

HREpCs were cultured in renal epithelial cell growth medium 2 (PromoCell, ready-to-use) supplemented with fetal calf serum (0.05 ml ml$^{-1}$) and Epidermal growth factor (10 ng ml$^{-1}$) Insulin (5 ug ml$^{-1}$), Epinephrine (0.5 ug ml$^{-1}$), Hydrocortisone (36 ng ml$^{-1}$), Transferrin, holo (5 ug ml$^{-1}$) and Triiodo-L-thyronine (4 μg ml$^{-1}$). 10 ml of complete medium was placed into T75 flask in the incubator in a humidified atmosphere of 5% $CO_2$, at 37° C. for 30 minutes. Cryopreserved HREpCs were placed in a 37° C. water bath for 90 s with constant agitation. The cells were pipetted up and down and then quickly transferred to the pre-warmed flask. The cells were incubated for a minimum of 16 hours before changing the medium. Subsequent media changes were performed every 2-3 days until the cells were confluent.

Cells were seeded with various concentrations of the polymers and the cell viability was determined with a MTT assay relative to a control with no polymer.

Minimal Inhibitory Concentrations (MICs) for Amphotericin Polymers

C. albicans cells, laboratory strain SC5314 or ATCC90028, were cultured on solid BHI (Oxoid) medium at 37° C. for 24 hours and stored at 4° C. for up to one month. Prior to experiments, a colony of C. albicans was sub-cultured into liquid BHI medium overnight at 37° C. Overnight cultures of C.albicans were adjusted to an optical density at 600 nm of 0.1 and incubated with Amphotericin polymers, which were serially diluted 1:2 from 2500-2.44 μg/ml, for 16 hours in a 96 well plate. The concentration of polymer at which there was no visible growth was determined to be the MIC. C.albicans (Robin) ATCC200955, C.tropicalis ATCC200956, A.flavus ATCC16883 and F. keratoplasticum ATCC36031 were similarly cultured on solid Sabrauds (Oxoid) medium at 37° C. for 24 hours and stored at 4° C. for up to one month. Prior to experiments, colonies were sub-cultured into liquid Sabrauds medium overnight at 37° C. All liquid cultures were static apart from A.flavus which was incubated shaking at 100 rpm.

Solubility of Branched-PNIPAM-Amp

Solutions of up to 300 mg ml$^{-1}$ of Branched-PNIPAM-Amp were found to be stable for 24 hours on a workbench. In the same timeframe solutions of 400 mg ml$^{-1}$ fully dissolved but became a viscous gel.

Analysis of Amphotericin

Figure 1:
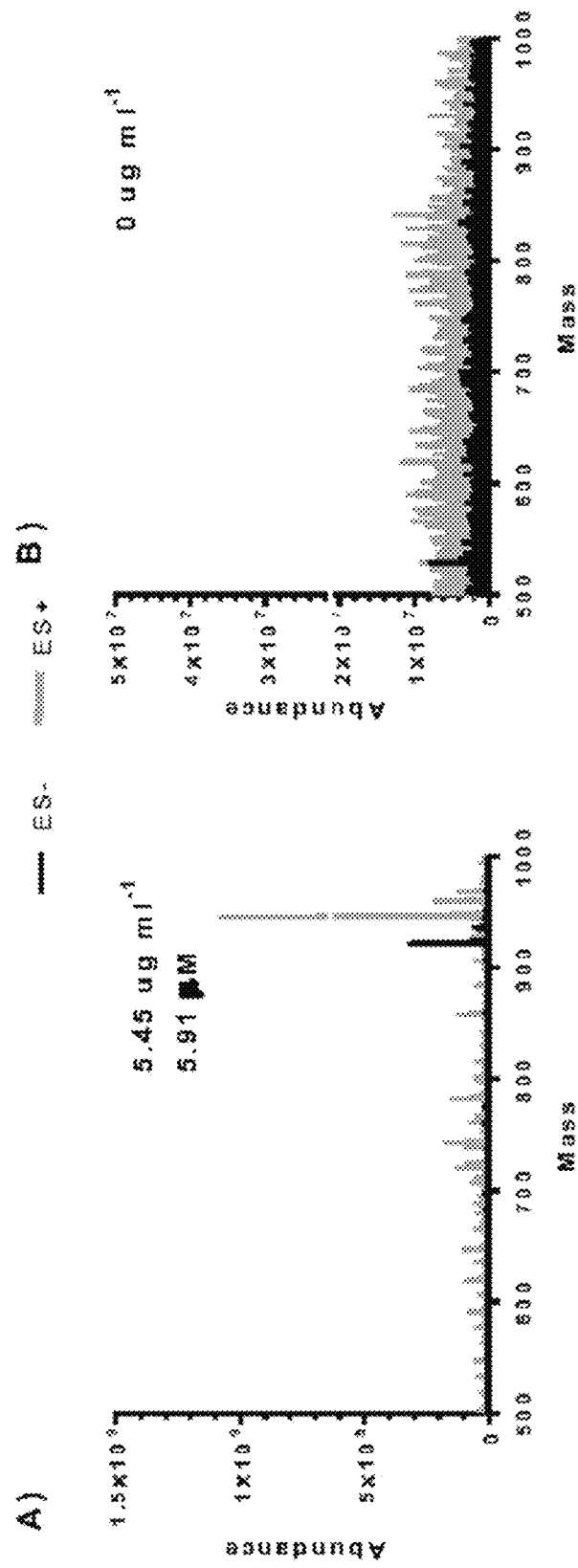
Figure 1:
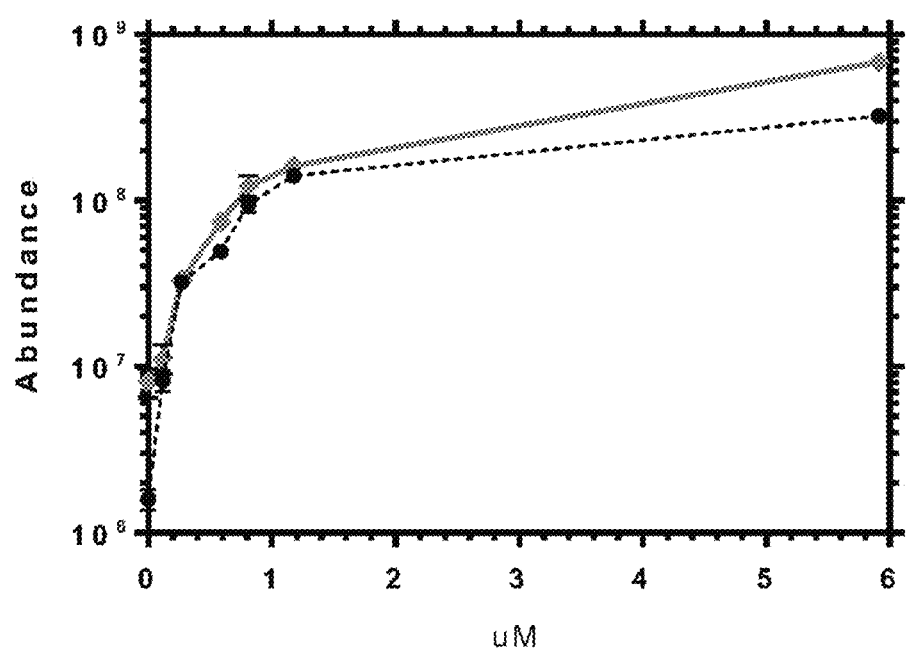
Figure 2:
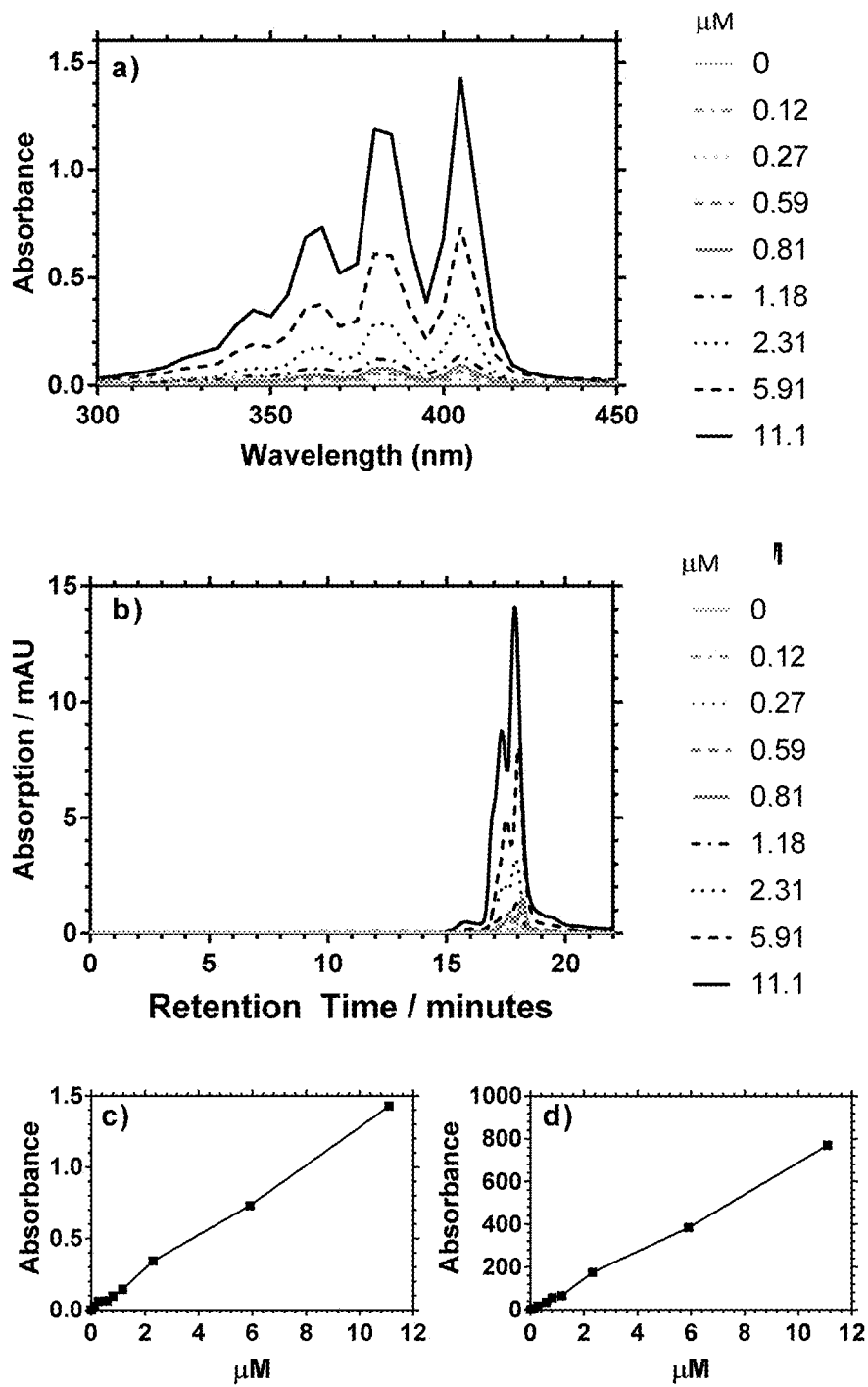
Figure 2:
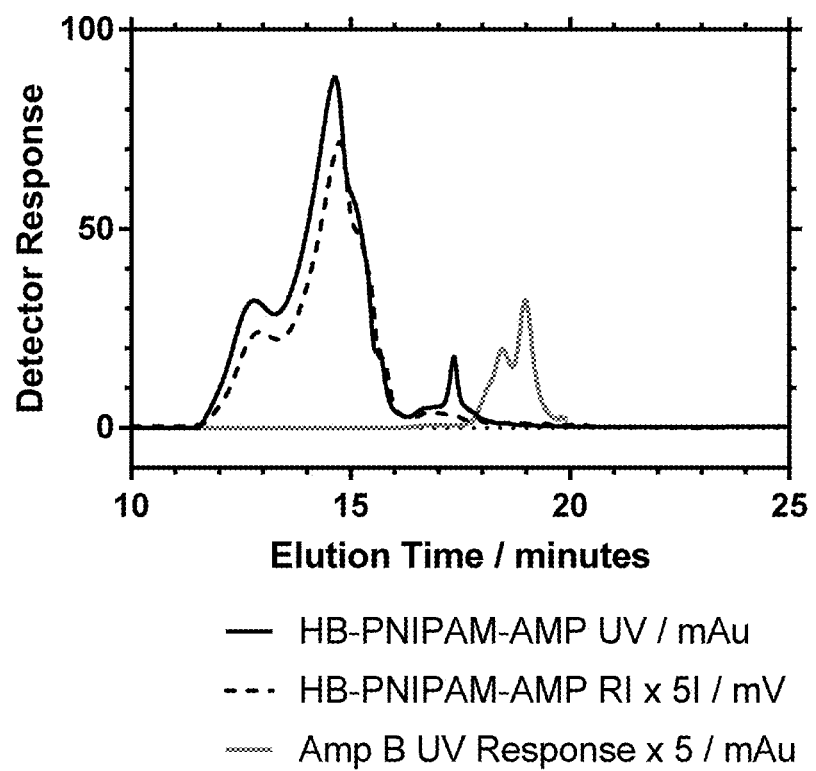

The purity of Amphotericin B used in the synthesis and for calibration of UV absorbance detectors was confirmed using HPLC-MS following several previous published protocols.[14] The material was a mixture (geometric isomers) of polyenes of similar mass with m/z 922 (see supporting information). The MIC for amphotericin B is 4.68-150 μM[19] and so a method of detection for free drug needed to be established which was sensitive below this concentration to ensure no residual unattached active agent remained post polymer functionalisation. This was carried out via two methods; firstly direct injection via mass spectroscopy (FIG. 1) and gel permeation chromatography (GPC) with detection by UV absorbance (FIG. 2).

Calibration measurements of low concentration Amphotericin B in methanol were undertaken to determine the lower limit of detection of the drug via direct injection electrospray mass spectrometry. FIG. 1 presents the data via both ES+ and ES− and clear peaks from the drug were observed at 922 and 947 m/z respectively. Greater fragmentation was observed in the ES+ mode giving significant peaks at 648 and 620 alongside greater residual noise. It was found that the mass spectrometer was sensitive to concentrations down to 0.27 μM, far below the target concentration. When the determination was used to examine the concentration of free Amp B in the polymer sample no Amp B could be detected. This test was repeated in the presence of non-functionalised polymers and only a slight reduction in sensitivity was observed.

Due to its high extinction coefficient an alternative measurement of Amp B was made using UV absorbance. The molar absorption coefficient was found to be the same via whole-solution absorbance and via the in-line GPC detector (9×10$^{11}$ mol$^{-1}$ cm$^{-1}$) (FIG. 2). For both methods, the same limit of detection (0.27 μM) was observed. FIG. 2 compares the chromatogram of an Amp B functional polymer to free Amp B. The retention time for Amp B is clearly seen but this peak is absent in the polymer sample.

Culture of Bacteria and Fungi

All experimental work was performed on rabbit corneas in the UK and on human corneas in India. For rabbit cornea infection models, the laboratory strains of Staphylococcus aureus (S-235), Pseudomonas aeruginosa (SOM-1), Candida albicans (SC5314) and Fusarium solani (NCPF 2699), purchased from the National Collection of Pathogenic Fungi (UK), were used. For work on human corneas, S. aureus ATCC 25923, P. aeruginosa (ATCC 27853) and C. albicans ATCC 90028 were used. All bacterial and fungal strains were cultured on brain heart infusion (BHI, Oxoid, UK) agar at 37° C. overnight and then maintained at 4° C. For use in experiments, one colony from agar plates was sub-cultured overnight at 37° C. in BHI broth and stationary phase microbes were used in experiments.

Isolation and Culture of Rabbit and Human Ex Vivo Corneas

The isolation and ex vivo culture of rabbit and human corneas was performed as described previously.[18] In summary the corneal-scleral buttons were placed epithelial side down in 35 mm petri-dishes and approximately 500 µl Dulbecco's Modified Eagle's Medium (DMEM)-agarose (0.5% w/v) solution was pipetted into the endothelial side of the cornea. The solution was allowed to solidify and then buttons were carefully inverted, so the epithelium was facing up. Culture medium, containing DMEM: Ham's F12 (1:1) supplemented with 10% FCS, 100 U ml$^{-1}$penicillin and 100 U ml$^{-1}$ streptomycin, 2.5 µg ml$^{-1}$ amphotericin B, 5 µg ml$^{-1}$ insulin, 10 ng ml$^{-1}$ EGF, was added in sufficient volume to submerge the corneas. Prior to infection, the corneas were washed three times with phosphate buffered saline (PBS) and incubated in antibiotic and antifungal-free medium for at least 24 hours to remove residual antimicrobials.

Infection of Ex Vivo Corneas

To introduce infection, corneas were wounded with a scalpel (3 cuts vertically and 3 cuts horizontally), and a metal ring was placed on the corneal-scleral button to surround the wounded areas and to create a watertight seal. In the centre of the ring 10$^8$ *S. aureus, P. aeruginosa, C. albicans* or *F. solani* were added in PBS. The corneas were then incubated for 24 or 48 h at 37° C. after which they were washed in PBS, homogenised for 1 min in a tissue homogeniser and the number of recovered organisms enumerated by colony counting.

Results and Discussion

Polymer Synthesis and Characterisation

Highly branched poly(N-isoproylacrylamide) with a high concentration carboxylic acid end groups was synthesised via the method reported previously[20] using self-condensing vinyl reversible addition fragmentation transfer polymerisation (SCVP-RAFT) in the presence of a vinyl functional benzyl dithioate ester (4-vinylbenzyl-pyrrolecarbodithioate, VPC) which acted as a branching agent, producing polymer with pyrrole end groups (Branched-PNIPAM-Py). The ratio of NIPAM:VPC in the monomer feed was 25:1 The final conversion of monomer was 95%. The chain ends were then modified to carboxylic acid and amidated with amphotericin B (Amp-B) via activation of the end groups as the succinimidyl ester. The reaction was carried out at pH 11 to fully solubilise the Amp-B. The Branched-PNIPAM-Amp was purified by repeated precipitation into diethyl ether, and then ultrafiltration in water through a 10 kDa membrane filter to retain only high molar mass material. The feed, molar mass averages and functionality are set out in Table 1.

TABLE 1

Synthesis of Branched-PNIPAM-Amp polymers; Feeds in the functionalisation reactions, molar masses and functionalities.

| Branched-PNIPAM/g | Amp-B/g | $M_n^a$ | $M_w^a$ | $M_z^a$ | $F^b$ |
|---|---|---|---|---|---|
| 1.00 | 0.03 | 8,534,100 | 8,990,250 | 1.05 | 18.3% |

Figure 3:
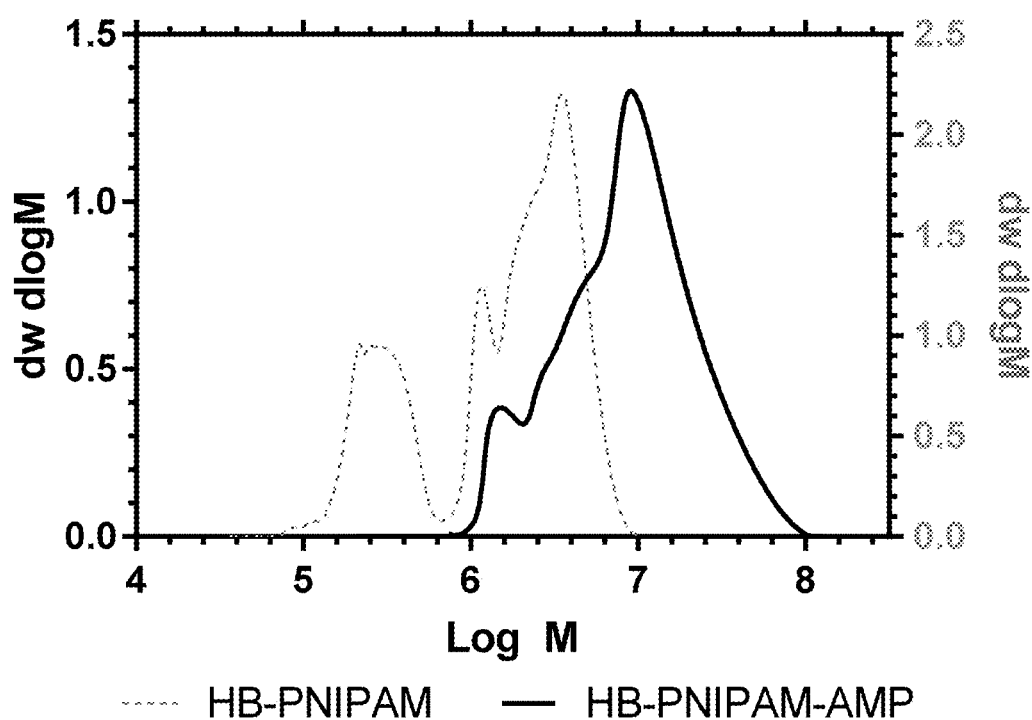
FIG. 3 shows the Molar Mass Distribution of Branched-PNIPAM-Amp.

$^a$Molar masses (kg mol$^{-1}$) were obtained by gel permeation chromatography in methanol.
$^b$Functionality (F) expressed as molar percentage of chain ends carrying an Amp-B moiety Additional reactions were carried out with increased feeds of Amp-B. However, feeds in excess of that shown provided polymer material contaminated with free Amp-B and this was difficult to remove. Branched-PNIPAM-Amp produced by this procedure and after multiple precipitations and ultra-filtration cycles is a high molar mass material with broad polydispersity. This is illustrated by the molar mass distribution, derived from GPC, of Branched-PNIPAM-Amp, which is shown in FIG. 3.

Figure 4:
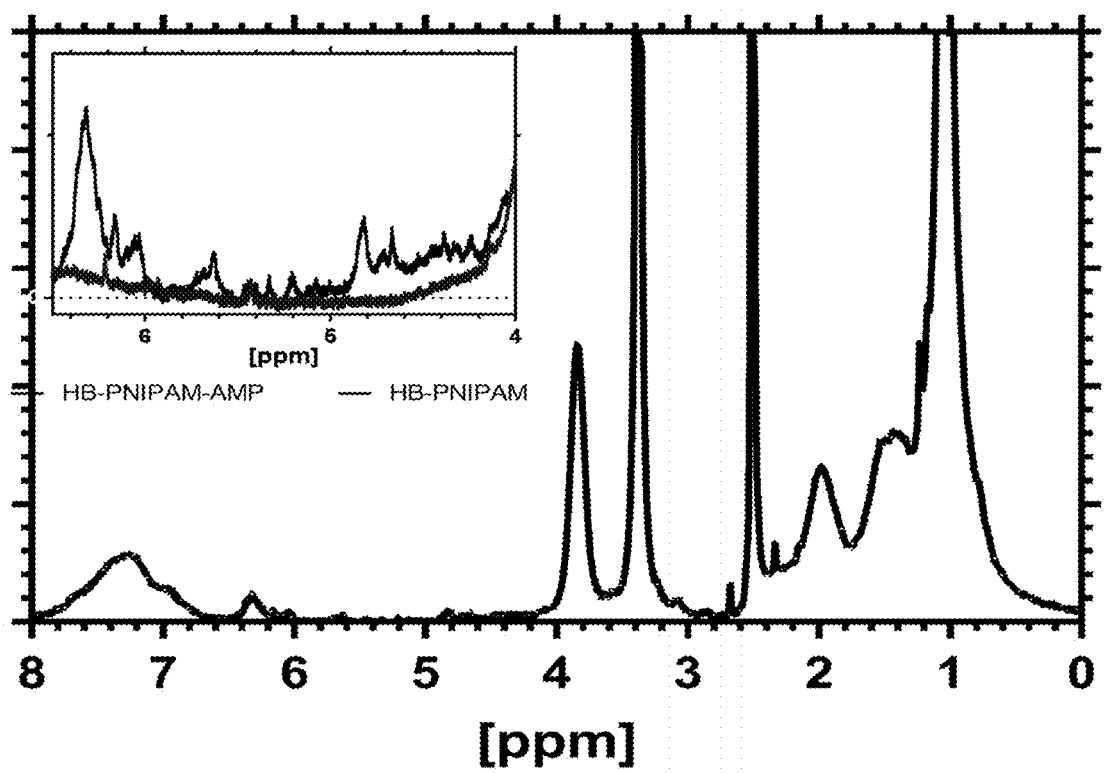
FIG. 4 shows the $^1$H NMR analysis of Branched-PNIPAM-Amp polymer with focus on 4-6 ppm (inset). Non-functionalised Branched-PNIPAM provided for reference.

The presence of amphotericin on polymer chains was demonstrated by $^1$H NMR spectroscopy as shown in FIG. 4. The functionalisation with Amp-B is demonstrated by the peaks arising between 4 and 6.5 ppm from the newly incorporated polyene ring.

DOSY NMR was also used to reveal the polymer hydrodynamic radii ($R_H$) distribution in DMSO[17] the spectrum is provided in the supporting information. This technique showed that $R_{H,n}$=2.55 nm and $R_{H,w}$=2.60 nm. The spectra also showed that within the limits of detection of the nmr technique the Branched-PNIPAM-Amp contained negligible amounts of Amp-B that was not attached to the polymer end groups. Mass spectrometry and UV absorbance at 405 nm was used to further examine the presence of residual Amp-B.

Mass Spectrometry of Branched-PNIPAM-Amp was carried out on a Micromass Quattro LC from Kinesis Solutions via direct injection of polymer into the detector (10 µg ml$^{-1}$) in spectroscopic grade methanol. It was determined that there was no free amphotericin within the polymer by the absence of peaks m/z 922 corresponding to Amphotericin B.

FIG. 1 shows: A) the mass spectrometry data of Amphotericin B in MeOH following direct injection (ES- black, ES+ grey) with varying concentrations; and B) border inserts average abundance response of detector to amphotericin injection (n=3).

UV absorbance measurements were carried out on Branched-PNIPAM-Amp samples and the concentration of amphotericin B determined via the Beer Lambert equation. FIG. 2 provides the in-line UV absorbance detector demonstrated that amphotericin B was equally distributed across the polymer molar mass distribution. This indicated that the polymer contained amphotericin functionality irrespective of the molar mass of the polymer. Also, no separate peaks were observed due to free amphotericin. Additional experiments were carried out using a Varian Cary 50 spectrometer and the total absorbance of the solution examined. The sum UV absorbance of the in-line detector and the solution gave equivalent molar absorption coefficients with respect to concentration.

The data confirms that Amp-B was successfully attached to the polymer chain ends via the succinimide reaction and that there were negligible amounts of residual Amp-B following the purification process.

Polymer Solution Properties

The solution properties of branched poly(N-isopropylacrylamides) are highly dependent on chain end effects as we have previously described.[21] The polymers are responsive to temperature and show a lower critical solution temperature (LCST) ($T_{crit}$). The $T_{crit}$ of these polymers (determined by calorimetry) are shown in Table 2 below. The data show that functionalisation with Amp-B led to an increase in $T_{crit}$.

TABLE 2

$T_{crit}$ of Branched-PNIPAM

| Polymer | $T_{crit}{}^a$ |
|---|---|
| Branched-PNIPAM-Py | 19.0 |
| Branched-PNIPAM-COOH | 22.2 |
| Branched-PNIPAM-Amp | 36.0 |

$^a$ Determined by microcalorimetry (1 mg ml$^{-1}$)

The $T_{crit}$ occurs at a coil-to-globule transition involving segmental desolvation and this can be monitored using the addition of solvatochromic fluorescence dyes such as nile red[15,21]. The emission wavelength of the nile red dye reflects the average internal polarity of the chain segments between the swollen and desolvated forms. Decreasing peak wavelength of the emission spectra indicates increasing hydrophobicity of the environment as it partitions into more hydrophobic (desolvated) domains. Nile red is thus a useful probe that can used to examine changes in the solvation of chain segments on binding of the end groups.

A solution of Branched-PNIPAM-Amp was mixed with nile red and studied both in the presence and absence of Ergosterol across a temperature range 5-45° C. (FIG. 5). The data shown in FIG. 5 showed a decrease in wavelength of nile red in with temperature in both the presence and absence of ergosterol when the dye was mixed with Branched-PNIPAM-Amp. However, at all temperatures the spectra shifted to lower wavelength on addition of ergosterol. Also, comparison of data obtained from Branched-PNIPAM-Amp to that obtained from Branched-PNIPAM-Py showed that the polymer with pyrrole end groups provided a much more desolvated environment at all temperatures and the data indicated that the $T_{cnt}$ occurred at around 19° C. in this polymer compared to the broad decrease in wavelength (24 to 40° C.) observed with Branched-PNIPAM-Amp. The data are thus in agreement with the increase in $T_{cnt}$ following modification to the provide the Amp-B end groups observed by calorimetry.

Therefore, these data indicate that on addition of ergosterol it binds to the Amp-B ligands at the chain ends of Branched-PNIPAM-Amp and this binding induces a segmental desolvation that reduces the average polarity of the environment into which nile red is portioned. The results show an interaction between the highly-branched polymer chain ends and the target ergosterol which will be located at the surfaces of fungi.

MICs for Branched-PNIPAM-Amp

Amp-B and Branched-PNIPAM-Amp were incubated with *C. albicans* to determine the minimal inhibitory concentration (MIC) (Table 3a). Only polymers containing the Amp-B drug were found to be effective against the fungi. The MIC of Amp-B was different for two different strains of *C. albicans*. However, there was little difference between the efficacy of the polymer to the two different strains. Importantly, the weight-based calculation of the MIC for the ATCC90028 strain was the same regardless of whether Amp-B or Branched-PNIPAM-Amp was used. The molar density of Amp B is 1.19 mmol g$^{-1}$ (M=838 g mold) and that of Branched-PNIPAM-Amp is 0.25 mmol g$^{-1}$. Therefore, on a molar basis the Amp-B is more effective against *C. albicans* strain ATCC90028 and the molar MIC against is approximately double that of Amp-B against strain SC5314. These figures indicate that Branched-PNIPAM-Amp could be an effective therapeutic agent against *C. albicans*. However, it is well known that Amp B is insoluble in water and saline solution at physiological pH. Conversely up to 300 mg ml$^{-1}$ of Branched-PNIPAM-Amp polymer can be dissolved before viscous gelation starts to occur. The increase in solubility of Branched-PNIPAM-Amp compared with Amp-B is a significant advantage for medical applications. Amp-B is also known to be highly toxic and is thus only used as "last resort" anti-fungal. Therefore, the two compounds were compared for their toxicity against rabbit limbal epithelial cells and human donor corneas to determine whether Branched-PNIPAM-Amp could be a viable and less cytotoxic alternative to the use of Amp-B.

Table 3b shows MIC values for Amp-B, Branched-PNIPAM-Py and Branched-PNIPAM-Amp for two Amp-B sensitive (SC5314, ATCC90028). and non-sensitive (ATCC200956, ATCC 200955) *Candida* strains, as well as for *Aspergillus flavus* ATCC16883 and *Fusarium keratoplasticum* ATCC36031, both Amp-B sensitive.

TABLE 3a

MIC values for Branched-PNIPAM-Amp and Amphotericin B for two *C. Albicans* strains

| Sample | MIC against SC5314 μg ml$^{-1}$ | MIC against ATCC90028 μg ml$^{-1}$ |
|---|---|---|
| Amphotericin B | 0.4 | 4 |
| Branched-PNIPAM-Py | >2500 | >2500 |
| Branched-PNIPAM-Amp | 4.9 | 4 |

TABLE 3b

MIC values for Amp-B, Branched-PNIPAM-Py and Branched-PNIPAM-Amp for various *Candida* strains, as well as for *Aspergillus flavus* ATCC16883 and *Fusarium keratoplasticum* ATCC36031

| | Weight based MIC*/μg mL | | | Molar MIC/μmol mL$^{-1}$ | | |
|---|---|---|---|---|---|---|
| | Amp-B | Branched-PNIPAM-Py | Branched-PNIPAM-Amp | Amp-B | Branched-PNIPAM-Py | Branched-PNIPAM-Amp |
| *C. albicans* SC5314 | 0.4 | >2500 | 4.9 | 0.5 | — | 1.2 |
| *C. albicans* ATCC90028 | 0.5 | >2500 | 4 | 4.8 | — | 1.0 |
| *C. albicans* ATCC200955 | >2500 | >2500 | >2500 | — | — | — |
| *C. tropicalis* ATCC200956 | >2500 | >2500 | >2500 | — | — | — |
| *A. flavus* ATCC 16883 | 1.5 | >2500 | 500 | 1.8 | — | 125 |
| *F. keratoplasticum* ATCC 36031 | 0.2 | >2500 | 6.25 | 0.25 | — | 1.6 |

*Molar densities Amp-B = 1.19 × 10$^{-3}$ μmol μg$^{-1}$; Branched-PNIPAM-Amp = 0.25 × 10$^{-3}$ μmol μg$^{-1}$ Cytotoxicity The metabolic activity of rabbit limbal epithelial cells in the presence of Amp-B and Branched-PNIPAM-Amp was determined. By assessing the reduction of Alamar Blue substrate, as the concentration of Amp-B increased there was a dose-dependent decrease in the metabolic activity of the cells, as shown in FIG. 6. There was a significant reduction ($p<0.01$) in the metabolic activity of cells after exposure to 100 µg ml$^{-1}$ Amp-B compared with the cell only control (42.8±13.9% and 100±7.1%, respectively), suggesting that a concentration of 100 µg ml$^{-1}$ would damage approximately half of cells in the area in which it was applied. For ophthalmic use, the main topical concentration of Amp-B used is approximately 1.5 mg ml$^{-1}$ [22]. At a concentration of 1 mg ml$^{-1}$ there was significant decrease ($p<0.01$) in epithelial cell viability of approximately 91.7% relative to a cell only control. Importantly, this level of loss in cell viability was not observed for Branched-PNIPAM-Amp, even at 5 mg ml$^{-1}$. This concentration is in excess of what is required for inhibiting the growth of C. albicans. Data suggests that weight for weight, amphotericin polymer is less 'toxic' to limbal epithelial cells than Amp-B.

The examination of the cytotoxicity was further examined on ex vivo human corneas. FIG. 7 shows that cellular toxicity was not observed for Branched-PNIPAM-Amp, where there was a large decrease for Amp-B. As Amp-B is topically applied to the cornea in instances of fungal keratitis, human donor corneas were exposed to Branched-PNIPAM-Amp (0, 2.5, 5, 10, 15, 20 mg ml$^{-1}$ in DMEM), for 48 hours and the biocompatibility determined using Alamar Blue. Only a loss of 20% viability was observed, even at very high concentrations of Branched-PNIPAM-Amp, e.g. 20 mg ml$^{-1}$. However, at concentrations of only 2.5 mg ml$^{-1}$ of Amp-B there was a significant loss of corneal viability ($p<0.01$), by approximately 95%. This indicated 2.5 mg ml$^{-1}$ amphotericin can damage a cornea, whereas Branched-PNIPAM-Amp allows a high dose treatment without corneal damage at concentrations greater than the MIC for fungi.

The assessment of cytotoxicity was further examined on human renal epithelial cells. The results are illustrated in FIG. 21.

Construction of Functional Hydrogels

Glycerol monomethacrylate (GMMA) (5 g, 4.660 ml), glycidyl methacrylate (GME) (0.345 g, 0.321 ml) and ethylene glycol dimethacrylate (EGDMA) (0.206 g, 0.196 ml) were degassed via bubbling dry nitrogen through solution whilst stirring in isopropanol (2 ml) for twenty minutes. 2-hydroxy-2-methylpropiphenone (HMPP) (55 mg) was added and the solution degassed for a further five minutes before it was extracted using a glass syringe and directly injected into a quartz plate mould separated with a 0.5 mm PTFE gasket. The two quartz plates were laminated with poly(ethylene teraphthalate) sheet, which was adhered to inner surfaces of the glass, to aid the release of the produced polymer sheet. To initiate polymerisation the mould was irradiated by a 400 w metal halide UV-A lamp for 3 minutes before being turned over and irradiated on the alternate side for a further 3 minutes. The cured hydrogel sheet was then removed and immersed in isopropanol. The hydrogel sheet was washed a total of five times with fresh isopropanol and left for at least 1 hour each time before being added to a 1,3-diaminopropane in isopropanol (20% v/v, 250 ml) solution for 48 hours, being inverted half way through. It was then washed and immersed for 1 hour in isopropanol a further two times. The hydrogel was characterised by measurement of equilibrium water content (EWC=61%, SD=4%, n=12). Fourier Transform Infrared spectroscopy (FTIR) was used to analyse for residual monomer leaching and the material was imaged using scanning electron microscopy and shown to provide a flat, uniform, crack free surface.

Hydrogel with Single Functionalised Polymer (Branched-PNIPAM-Van, Branched-PNIPAM-PMX or Branched-PNIPAM-Amp)

Aminated hydrogels were exposed to Branched-PNIPAM-Amp (50 mg) and dissolved in isopropanol (100 ml). The hydrogel sheets (90×90×0.5 mm) were immersed for 48 hours on a low speed shaker with inversion after 24 hours. Following the reaction, it was washed twice with pure isopropanol and left for one hour each time. Polymer films were characterised by assessing equilibrium water content (EWC) (see Table 4) and FTIR. Drug loading on these sheets was determined by both an amphotericin ELISA of hydrogel discs, where multiple samples (n=9) were analysed, and also via the UV absorbance of a cross section of the hydrogel sheet where a distinct increased absorption for amphotericin was observed at 550 nm (see FIG. 19 and FIG. 20), and this increase could be correlated back to drug loading.

Hydrogel Functionalised with Branched-PNIPAM-Van, Branched-PNIPAM-PMX and Branched-PNIPAM-Amp The aminated hydrogel (90×90×0.5 mm) was exposed to Branched-PNIPAM-Van (50 mg), Branched-PNIPAM-PMX (100 mg) and Branched-PNIPAM-Amp (60 mg) dissolved in isopropanol (100 ml). Hydrogels containing other amounts are disclosed in the supporting information. These are identified as triple functional hydrogels in this work. The hydrogel sheet was left immersed in this mixture for 48 hours on a slow speed shaker and the hydrogel inverted half way through. When the polymers had reacted, they were washed with isopropanol for one hour. The isopropanol was refreshed, left for a further hour and removed before 20 ml of piperidine in isopropanol (20% v/v) was added to the hydrogel sheet. This was allowed to react for 48 hours before being washed in pure isopropanol for another hour, three further times. Prior to use all hydrogels were washed three times in PBS and then incubated in media.

TABLE 4

Characterisation data of the prepared hydrogels

| Reference | Feed of HB-PNIPAM-X/mg 5 g$^{-1}$* | | | | Functionality/ug mg$^{-1}$ | | | Water content/ |
|---|---|---|---|---|---|---|---|---|
| | COOH | Van | PMX | Amp | Van*** | PMX**** | Amp*** | wt % |
| HB-PNIPAM-COOH | 30 | 0 | 0 | 0 | 0 | 0 | 0 | 59% |
| HB-PNIPAM-Van | 0 | 30 | 0 | 0 | 102 | 0 | 0 | 51% |
| HB-PNIPAM-PMX | 0 | 0 | 30 | 0 | 0 | 95 | 0 | 49% |
| HB-PNIPAM-Amp | 0 | 0 | 0 | 60 | 0 | 0 | 100 | 60% |

TABLE 4-continued

Characterisation data of the prepared hydrogels

| | Feed of HB-PNIPAM-X/mg 5 g$^{-1}$* | | | | Functionality/ug mg$^{-1}$ | | | Water content/ |
|---|---|---|---|---|---|---|---|---|
| Reference | COOH | Van | PMX | Amp | Van*** | PMX**** | Amp*** | wt % |
| Dual-Functionalised** | 0 | 30 | 30 | 0 | 86 | 100 | 0 | 53% |
| Triple-Functionalised A | 0 | 30 | 36 | 60 | 105 | 100 | 450 | 55% |

In Vitro Interaction of Microorganisms with Polymer-Linked Hydrogels $10^8$ FITC labelled S. aureus, P. aeruginosa or C. albicans were incubated in vitro with vancomycin-, polymyxin- or amphotericin-functionalised hydrogels respectively or triple hydrogels (all three agents) for 1 hour. Hydrogels were washed 3 times with PBS, then imaged using a fluorescence microscope (Axiovert 200M, Zeiss) and the imaging software AxioVision Rel. 4.8 in UK and ProgRes CapturePro 2.5 software (Jenoptik) in India.

Detection of Bacteria and Fungi from Infected Rabbit and Human Corneas by Attaching to the Triple-Functional Hydrogel Triple functionalised hydrogels were placed onto rabbit and human corneas that had been infected with $10^8$ S. aureus, P. aeruginosa or C. albicans and left in place for 60 min. with Calcofluor white using a 1:1 solution of Calcofluor white ready to use solution and 10% potassium hydroxide for visualisation of fungi. Prior to staining with fluorescent vancomycin or FITC, hydrogels were reacted with 0.1% periodic acid (Sigma) for 10 min, washed ×2 with PBS and then incubated with Schiff's reagent for 10 min before washing ×2 again and viewing with a fluorescence microscope. Hydrogels were incubated with vancomycin Bodipy®FL conjugate (2 µg ml$^{-1}$; FL-Vanc; ThermoFisher), for visualisation of Gram-positive (S. aureus) organisms, then with FITC (0.5 mg ml$^{-1}$) for Gram-negative organisms (P. aeruginosa). After incubation for 10 min the hydrogels were washed 3× in PBS.

Assessment of the Limit of Attachment of Microbes

To assess the sensitivity of the functionalised hydrogels increasing numbers of S. aureus, P. aeruginosa or C. albicans were incubated in vitro with triple-functionalised hydrogels for 1 hour. The hydrogels were washed and the total ATP content determined using the ENLITEN® ATP assay kit according to the manufacturer's instructions.

In another set of experiments increasing numbers of each organism were incubated in vitro with triple functionalised hydrogels for 1 hour. Hydrogels were washed and then examined with a fluorescence microscope and the number of organisms per field of view counted. The data were compiled as mean±SD of 8 fields of view per hydrogel from at least 3 independent experiments Determination of the Optimal Time of Placement of the Hydrogel on the Infected Cornea Ex vivo human corneas were infected with S. aureus, P. aeruginosa, C. albicans and F. solani for 24 hours, washed and exposed to a triple functionalised hydrogel for different time intervals of 60, 30 and 15 min. Microorganisms bound to the hydrogels were detected using the protocol described above.

Statistical Significance

The attachment of bacteria/fungi to the triple hydrogels was compared using a one-way ANOVA with Dunnett's multiple comparison ($p < 0.05$ comparing 0 and $10^8$ only).

Attachment of Organisms to Hydrogels

Interaction and Attachment of Organisms to Hydrogels with Single Functionalised Polymer in in-Vitro Experiments Before assessment of a triple-functional hydrogel for binding Gram-positive, −negative bacteria and fungi, it was important to establish the binding capability of each polymer-linked hydrogel in turn.

We have reported previously that PNIPAM-hydrogels funtionalised with vancomycin could bind Gram-positive bacteria and a similar material funcionalised with a polymyxin-functional polymer bound a Gram-negative species [23] but here a different hydrogel base was employed. GMMA-hydrogels with linked Branched-PNIPAMs funtionalised with either vancomycin, polymyxin or amphotericin B were exposed to the respective microorganisms. As shown with the previous system the functionalised surface with grafted Branched-PNIPAM can bind microbial species both effectively and selectively (FIG. 10).

Binding of Microorganisms to Functionalised Hydrogels.

$10^8$ FITC labelled S. aureus, P. aeruginosa or C. albicans were incubated in vitro with vancomycin, polymyxin or amphotericin functionalised GMMA-hydrogels or with the triple functionalised hydrogel (all three polymers combined in one hydrogel together) respectively for 1 hour. Hydrogels were washed 3×PBS and imaged using a fluorescence microscope. 8 fields of view were imaged and the number of organisms attaching to the hydrogels per field of view (FIG. 11) were analysed using Image J. The number of organisms attaching to the functionalised hydrogels was compared with a non-functionalised hydrogel. Bars indicate mean±SEM of 8 fields of view analysed from at least 3 independent experiments Representative examples of images of S. aureus, P. aeruginosa and C. albicans attached to the surface of the triple hydrogel and to the non-functionalised control hydrogel are shown in FIG. 12.

FIG. 12 shows the optical micrographs of bacteria and fungi bound to hydrogel surfaces. $10^8$ S.aureus, P.aeruginosa or C. albicans were incubated for 1 hour in vitro with the triple polymer-functionalised hydrogel compared to the non-functionalised control hydrogels. S.aureus and P.aeruginosa bound hydrogels were incubated with periodic acid and Schiff's reagent and then stained with fluorescently labelled -Vancomycin and FITC respectively. C.albicans bound hydrogels were stained with Calcofluor white. All hydrogels were imaged using a fluorescence microscope. Images shown are representative examples of 8 fields of view.

Determination of the Limit of Detection of the Triple Hydrogel

The results of a study using the determination of the amount of ATP present by luminescence are shown in FIG. 13. There was an increase in level of luminescence with increasing numbers of S.aureus, P.aeruginosa or C.albicans. A significant difference was observed with $10^5$ organisms of S. aureus; $10^6$ of P. aeruginosa and $10^3$ of C. albicans.

Increasing numbers of S. aureus, P. aeruginosa or C. albicans were incubated in vitro with triple (vancomycin, polymyxin and amphotericin polymer) functionalised hydrogels for 1 hour. Hydrogels were washed and the total ATP content analysed using the ENLITEN® ATP assay kit according to manufacturer's instructions. Graphs show mean±SEM of three independent experiments. The attachment of bacteria/fungi to the triple hydrogels was compared using a one-way ANOVA with Dunnett's multiple comparison ($p<0.05$ comparing 0 and $10^8$ only). The result may be seen in FIG. 13A.

In a second set of experiments wherein we counted the number of organisms attached to the hydrogel we observed identical trends i.e. increasing number of attached organisms with increased load of incubation. Exposure to equal to or greater than $10^4$ organisms resulted in significantly higher number of attached organisms than those attached to non-functionalised hydrogels. (FIG. 13B)

Determination of how Long the Triple Hydrogels Needs to be on the Cornea

FIG. 14 shows *S. aureus*, *P. aeruginosa*, and *C. albicans* cells adherent to the surface of the triple hydrogel at different time points. Higher loads of organisms were observed with increased duration of application of the hydrogel. It was also noticed that 30 minutes of exposure gave a reasonable load of microorganisms.

FIG. 14: Representative images (A) of triple functionalised hydrogels removed from infected human corneas and stained, and the number of organisms recovered in culture from hydrogels. Human corneas were mono-infected with *S. aureus*, *P. aeruginosa* and *C. albicans* and triple-functionalised hydrogels were placed on to the corneas and left in place for either 15, 30 or 60 minutes. The hydrogels were then stained using fluorescent vancomycin, FITC or calcofluor white as described in the methods.

FIG. 15 shows the enumeration of *S. aureus*, *P. aeruginosa* and *C. albicans* infections detected using a triple functionalised hydrogel. Ex vivo human corneas were infected with *S. aureus*, *P. aeruginosa* or *C. albicans* for 24 hours, washed and exposed to a triple functionalised bacterial hydrogel for 60 min, 30 min and 15 min. Hydrogels with *S. aureus* were detected using fluorescent vancomycin and hydrogels with *P. aeruginosa* were detected using FITC. Both hydrogels were counter-stained using periodic acid and Schiff's reagent prior to staining. Hydrogels with *C. albicans* and *F. solani* were detected using Calcofluor White. Images show the per field view count of *S. aureus*, *P. aeruginosa* and *C. albicans* bound to hydrogels removed from infected ex vivo corneas.

A second, separately synthesised batch of triple hydrogels were also tested for binding the test microorganisms to validate the above conclusion that 30 min exposure was an adequate time. Similar data were obtained using this second batch of hydrogels (see FIG. 16)

FIG. 16 shows *S. aureus*, *P. aeruginosa*, *C. albicans* and *F. solani* infections detected using a triple functionalised hydrogel. Ex vivo human corneas were infected with *S. aureus*, *P. aeruginosa*, *C. albicans* or *F. Solani* for 24 hours, washed and exposed to a triple functionalised bacterial hydrogel for 30 min. Hydrogels with *S. aureus* were detected using fluorescent vancomycin and hydrogels with *P. aeruginosa* were detected using FITC. Both hydrogels were blocked using periodic acid and Schiff's reagent prior to staining. Hydrogels with *C. albicans* and *F. solani* were detected using Calcofluor White. Images show *S. aureus*, *P. aeruginosa* and *C. albicans* bound to hydrogels removed from infected ex vivo corneas.

FIG. 17 shows *S. aureus*, *P. aeruginosa*, *C. albicans* and *F. solani* infections detected using a triple functionalised hydrogel. *S. aureus*, *P. aeruginosa*, *C. albicans* and *F. solani* infections detected using a triple functionalised hydrogel. Ex vivo human corneas were infected with *S. aureus*, *P. aeruginosa*, *C. albicans* or *F. Solani* for 24 hours, washed and exposed to a triple functionalised bacterial hydrogel for 30 min. Hydrogels with *S. aureus* were detected using fluorescent vancomycin and hydrogels with *P. aeruginosa* were detected using FITC. Both hydrogels were blocked using periodic acid and Schiff's reagent prior to staining. Hydrogels with *C. albicans* and *F. solani* were detected using Calcofluor White. Images show the per field view count of *S. aureus*, *P. aeruginosa* and *C. albicans* bound to hydrogels removed from infected ex vivo corneas. The number of organisms in the infected corneas as determined after homogenisation of the corneal tissue was similar to values previously reported.[19]

The microbial loads ranged from $5\times10^7$ to $5\times10^4$ in the order *S. aureus*, *P. aeruginosa*, *C. albicans* and *F. solani* going from the most numerous to the least numerous.

FIG. 18 shows the number of CFU recovered from infected corneas. *S. aureus*, *P. aeruginosa*, *C. albicans* or *F. Solani* for 24 hours, washed and exposed to a triple functionalised bacterial hydrogel for 30 min are then homogenised, the solution serially diluted and plated on agar plates to determine the number of CFUs per cornea. Data shows a box and whisker plot of the number of CFU recovered per cornea.

EXAMPLE 2—IN VIVO EVALUATION OF A "TRIPLE HYDROGEL" COMPRISING BRANCHED PNIPAM-AMP CONJUGATES ALONG WITH CONJUGATES OF BRANCHED PNIPAM-PMX AND BRANCHED PNIPAM-VAN

The objective of the study was to determine the diagnostic sensitivity and specificity of "Triple-Hydrogels" in the detection of infection in corneal infection models using New Zealand White Rabbits.

Methodology and Experimental Design:

Forty albino white rabbits weighing 2-2.5 kg each were randomly distributed into five groups of eight each.

| Group | Treatment | No. of Animals |
|---|---|---|
| G1 | Test item-Gram negative-*Pseudomonas aeruginosa* | 8 |
| G2 | Test item-Gram positive-*Staphylococcus aureus* | 8 |
| G3 | Test item-Fungi-*Candida albicans* | 8 |
| G4 | Test item-Mixed infection (Gram positive + Fungi) & (Gram negative + Fungi) | 8 |
| G5 | Test item-Gram negative-*Pseudomonas aeruginosa* repeat | 8 |

Animals were anesthetised using a combination of ketamine (40 mg/kg B. wt.) and xylazine (10 mg/kg B.wt) approximately 10 minutes before administration of inoculum. The prepared 100 µL bacterial suspension was injected intrastromally into the centre of the cornea of each rabbit. Animals from G3 and G4 were also given 500 µL of Triamcinolone Acetonide and Dexamethasone sodium phosphate in the bulbar conjunctiva just before injecting *Candida albicans*. This protocol could sustain active corneal infection and allows highly reproducible infection.

Following development of ulcers, the animals were anesthetised using a combination of ketamine (40 mg/kg B. wt.) and xylazine (10 mg/kg B.wt). Hydrogels were kept on the infected corneas. Immediately after the application, the eyes were closed for 30 min while the animals were maintained under anaesthetic. After 30 min of application the hydrogels were taken out using separate sterile forceps and transferred immediately into micro titter plate containing PBS. The fluorescent detection protocols used were based on the nature of the infection and the organisms were detected using a fluorescent microscope. To compare these results with conventional microbiology, we performed scraping of the infected corneas and sample was smeared on slides for conventional microscopic examination as well as plated onto Blood agar for culture.

Results

The results showed that the Gram +ve bacteria, Gram −ve bacteria and fungal cells all bound to the BDP-Triple hydrogel surface both in single and mixed infection models with counts of 43±15, 106±5 and 10±5 cells per field of view respectively. (FIGS. 8 and 9A). These could be identified using the staining protocols followed in this study and were similar to conventional microbiology results. No binding was observed on non-functionalised hydrogels.

Group 1 showed mixed infection with both Gram +ve and Gram −ve bacilli although the animals were inoculated with *Pseudomonas aeruginosa*. The results of the test device however, were similar to conventional microbiology. An impression of contamination was made.

The group 4 hydrogels were stained with bacterial staining (F-Vanc/FITC) first and then the same hydrogels were counter stained with fungal staining (Calcoflour white). Four animals of the group infected with Gram+ve bacteria and fungi were stained with F-Vanc and Calcoflour white. Our observations showed the presence of polymorphs, epithelial cells and cocci shaped clusters of bacteria with a count of 70±8 and budding yeast like cells with a count of 16±9 on an average per field view under the fluorescent microscope.

The other 4 animals in the group were infected with Gram-ye bacteria and *C. albicans*. The average no of organisms per field view were found to be 102±50 and 26±6 bacteria and fungi respectively (FIG. 9B)

Hydrogels kept on *S. aureus* infected rabbit cornea for 30 min, washed were blocked with Schiff's reagent and stained with fluorescent vancomycin and hydrogels added to a *P. aeruginosa* infected rabbit cornea were blocked with Schiff's reagent and stained with FITC. Hydrogels added to a *C. albicans* infected cornea were stained with Calcofluor White, without blocking. Further the stained hydrogels are imaged under fluorescent microscope.

CONCLUSION

In the in vivo experimental conditions of this study, BDP-Triple (Branched-PNIPAM-V/P/A functionalised GMMA hydrogel) was found to be sensitive and specific in the detection of micro-organisms in an animal model of corneal infection in the New Zealand white rabbit. Although the group 1 showed mixed infection with the test results these results were confirmed by conventional microbiology of corneal scrapings and the excised corneal buttons further substantiated the efficacy of the device in detecting causative microorganisms.

While specific embodiments of the invention have been described for the purpose of reference and illustration, various modifications will be apparent to a person skilled in the art without departing from the scope of the invention as defined by the appended claims.

REFERENCES

[1] P. D. H. Feldmann in *Yeast Cell Architecture and Functions*, Wiley-VCH Verlag GmbH & Co. KGaA, 2012, pp. 5-24.
[2] K. C. Gray, D. S. Palacios, I. Dailey, M. M. Endo, B. E. Uno, B. C. Wilcock and M. D. Burke, *Proceedings of the National Academy of Sciences* 2012, 109, 2234.
[3] J. Brajtburg, W. G. Powderly, G. S. Kobayashi and G. Medoff, *Antimicrobial Agents and Chemotherapy* 1990, 34, 183.
[4] L. Storm, K. R. Lausch, M. C. Arendrup, K. L. Mortensen and E. Petersen, *Medical Mycology Case Reports* 2014, 6, 6.
[5] A. Wong-Beringer, R. A. Jacobs and B. J. Guglielmo, *Clinical Infectious Diseases* 1998, 27, 603.
[6] Y. Nakagawa, Y. Umegawa, N. Matsushita, T. Yamamoto, H. Tsuchikawa, S. Hanashima, T. Oishi, N. Matsumori and M. Murata, *Biochemistry* 2016, 55, 3392.
[7] a) L. Jaimes-Aguirre, B. V. Gibbens-Bandala, E. Morales-Avila, B. E. Ocampo-Garcia, M. Seyedeh-Fatemeh and A. Amirhosein, *Current Pharmaceutical Design* 2016, 22, 2886-2903; b) T. C. M. M. Carraro, N. M. Khalil and R. M. Mainardes, *Pharmaceutical Development and Technology* 2016, 21, 140.
[8] a) P. Jansook, W. Pichayakorn, C. Muankaew and T. Loftsson, *Drug Development and Industrial Pharmacy* 2016, 42, 1446; b) C. Alvarez, D. H. Shin and G. S. Kwon, *Pharmaceutical Research* 2016, 1.
[9] a) A. Halperin, Y. Shadkchan, E. Pisarevsky, A. M. Szpilman, H. Sandovsky, N. Osherov and I. Benhar, *Journal of Medicinal Chemistry* 2016, 59, 1197; b) T. R. M. Tan, K. M. Hoi, P. Zhang and S. K. Ng, *PLoS ONE* 2016, 11, e0152112.
[10] N. E. Allen, D. L. LeTourneau, J, N. Hobbs, *J. Antibiotics*, 1997, 50, 677.
[11] S. S. F. Leung, J. Tirado-Rives, W. L. Jorgensen *Bioorganic & Medicinal Chemistry* 2009, 17, 5874.
[12] Magee et *J. Med. Chem* 2013, 56, 5079
[13] M. Vaara *J. Antimicrob Chemother* 2013, 68, 1213.
[14] S. Rimmer, S. Carter, R. Rutkaite, J. W. Haycock, L. Swanson, *Soft Matter*, 2007, 3, 971
[15] R. Plenderleith, T. Swift and S. Rimmer, *RSC Advances* 2014, 4, 50932.
[16] A. Lemke, A. F. Kiderlen and O. Kayser, *Applied Microbiology and Biotechnology* 2005, 68, 151.
[17] T. Swift, R. Hoskins, R. Telford, R. Plenderleith, D. Pownall and S. Rimmer, *Journal of Chromatography A* 2017, 1508, 16.
[18] A. Pinnock, N. Shivshetty, S. Roy, S. Rimmer, I. Douglas, S. Mac Neil, P. Garg Graefe's Arch. *Clin Exp. Opth.* 2017, 255, 333.
[19] a) V. Janout, W. A. Schell, D. Thévenin, Y. Yu, J. R. Perfect and S. L. Regen, *Bioconjugate Chemistry* 2015, 26, 2021-2024; b) D. E. Ickowicz, S. Farber, E. Sionov, S. Kagan, A. Hoffman, I. Polacheck and A. J. Domb, *Biomacromolecules* 2014, 15, 2079.
[20] P. Teratanatorn, R. Hoskins, T. Swift, C. W. I. Douglas, J. Shepherd and S. Rimmer, *Biomacromolecules* 2017, 18, 2887.
[21] T. Swift, J. Lapworth, K. Swindells, L. Swanson and S. Rimmer, R S C Advances 2016, 6, 71345.
[22] D. Al-Badriyeh, C. F. Neoh, K. Stewart and D. C. M. Kong in *Clinical utility of voriconazole eye drops in ophthalmic fungal keratitis,* 2010, 4, 391.
[23] J. Shepherd, P. Sarker, S. Rimmer, L. Swanson, S. MacNeil and I. Douglas, *Biomaterials* 2011, 32, 258.

The invention claimed is:
1. A hydrogel composition comprising
a polyacrylate-based hydrogel polymeric matrix formed from the reaction between glycerol monomethacrylate (GMMA), glycidyl methacrylate (GME) and ethylene glycol dimethacrylate (EGDMA); and
a first polymer conjugate, or a salt thereof, having the general formula:

$P\text{-}[Q]_x$ wherein:
P is a branched temperature-responsive polymer comprising a plurality of functional groups, and wherein one or more of said functional groups are covalently attached to a ligand capable of binding to ergosterol;
Q is a ligand capable of binding to ergosterol; and
x is the percentage of functional groups on the branched temperature-responsive polymer, P, that are attached to Q, wherein x is greater than or equal to 10%;
together with:
(i) a second polymer conjugate, or a salt thereof, having the general formula:

$P^1\text{-}[Q^1]_y$ wherein:
$P^1$ is a branched temperature-responsive polymer, comprising a plurality of functional groups, and wherein one or more of said functional groups are covalently attached to a ligand capable of binding to Gram positive bacteria;
$Q^1$ is a ligand capable of binding to Gram positive bacteria; and
y is the percentage of functional groups on the branched temperature-responsive polymer, $P^1$, that are attached to $Q^1$, wherein y is greater than or equal to 10%;
and/or
(ii) a third polymer conjugate, or a salt thereof, having the general formula:

$P^2\text{-}[Q^2]_z$ wherein:
$P^2$ is a branched temperature-responsive polymer, comprising a plurality of functional groups, and wherein one or more of said functional groups are covalently attached to a ligand capable of binding to Gram negative bacteria;
$Q^2$ is a ligand capable of binding to Gram negative bacteria; and
z is the percentage of functional groups on the branched temperature-responsive polymer, $P^2$, that are attached to $Q^2$, wherein z is greater than or equal to 10%;
wherein:
P is branched poly(N-isopropylacrylamide) and Q is amphotericin B, nystatin or natamycin;
$P^1$ is branched poly(N-isopropylacrylamide) and Q1 is vancomycin; and
$P^2$ is branched poly(N-isopropylacrylamide) and Q2 is polymyxin B;
wherein the first polymer conjugate, the second polymer conjugate and the third polymer conjugate are covalently attached to the polyacrylate-based hydrogel polymer matrix;
and wherein the polyacrylate-based hydrogel polymer matrix comprises greater than 50% w/w of water.

2. The hydrogel composition according to claim 1, wherein the hydrogel composition comprises a first polymer conjugate of the formula $P\text{-}[Q]_x$ and either a second polymer conjugate of the formula $P^1\text{-}[Q^1]_y$ or a third polymer conjugate of the formula $P^2\text{-}[Q^2]_z$ or a salt thereof.

3. The hydrogel composition according to claim 1, wherein the hydrogel composition comprises a first polymer conjugate of the formula $P\text{-}[Q]_x$, a second polymer conjugate of the formula $P^1\text{-}[Q^1]_y$, and a third polymer conjugate of the formula $P^2\text{-}[Q^2]_z$ or a salt thereof.

4. The hydrogel composition according claim 1, wherein any one or more of x, y, and z is greater than or equal to 50%.

5. The hydrogel composition according to claim 1, wherein each Q, $Q^1$ or $Q^2$ group present is bound to a terminus of one of the branches of the polymer P, $P^1$ or $P^2$ respectively by the reaction of a terminal carboxy group present on P, $P^1$ or $P^2$ with an amine group present on Q, $Q^1$ or $Q^2$ to form a —C(O)—NH— linking group.

6. The hydrogel composition according to claim 1, wherein P, $P^1$ or $P^2$ is a temperature-responsive polymer having branches occurring at every 10 to 25 monomer units.

7. The hydrogel composition according to claim 1, wherein P, $P^1$ or $P^2$ is temperature-responsive polymer formed from: A) N-isopropylacrylamide; and B) one or more branching agents selected from 4-vinylbenzyl-pyrrolecarbodithioate (VPC), vinylbenzyl-phenylcarbodithioate, vinylbenzyl imidazoledithioate, vinylbenzyl alkyldithoates, and derivatives thereof.

8. The hydrogel composition according claim 7, wherein the branching agent is 4-vinylbenzyl-pyrrolecarbodithioate (VPC).

9. The hydrogel composition according to claim 1, wherein Q is amphotericin B.

10. The hydrogel composition according to claim 1, wherein the first polymer conjugate $P\text{-}[Q]_x$ has the formula:

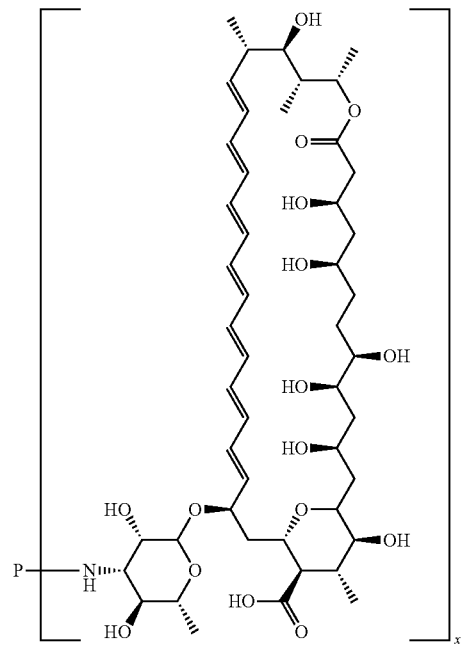

wherein the group in the square brackets is amphotericin B, P is branched poly(N-isopropylacrylamide);
wherein each amphotericin B molecule is bound to a terminus of the branched poly(N-isopropylacrylamide) molecule, and x is greater than or equal to 50%.

11. The hydrogel composition according to claim 9, wherein the water content of the hydrogel is greater than 70% w/w, or greater than 90% w/w.

12. A contact lens, membrane, swab or wound dressing comprising the hydrogel composition according to claim 1.

13. A method of detecting the presence of fungal cells, Gram positive bacterial cells and/or Gram negative bacterial cells in a sample, the method comprising:
(i) contacting the hydrogel composition according to claim 1, or a contact lens, membrane, swab or wound dressing comprising the hydrogel composition according to claim 1 with the sample;
(ii) removing either the hydrogel composition, contact lens, membrane, swab or wound dressing from the sample and testing for the presence of bound fungal cells, Gram positive bacterial cells and/or Gram negative bacterial cells.

14. The method of claim 13, wherein presence of fungal cells, Gram positive bacterial cells and/or Gram negative bacterial cells attached to the polymer conjugates present in the hydrogel composition is detected by microscopy/histological assessment, staining and microscopy techniques, or physically removing bound cells and culturing them.

15. A method of determining the presence of a fungal, Gram positive bacterial and/or Gram negative bacterial infection and/or diagnosing a fungal, Gram positive bacterial and/or Gram negative bacterial infection, the method comprising:
(i) contacting the hydrogel composition according claim 1, or a contact lens, membrane, swab or wound dressing comprising the hydrogel composition according to claim 1 with either a sample obtained from the suspected site of infection or with the suspected site of infection directly; and
(ii) detecting the presence of any a fungal, Gram positive bacterial and/or Gram negative bacterial cells attached to the hydrogel composition, contact lens, membrane, swab or wound dressing and optionally determining the type of fungi, Gram positive bacteria and/or Gram negative bacteria detected.

16. The method of claim 15, wherein presence of fungi, Gram positive bacteria and/or Gram negative bacteria is detected by microscopy/histological assessment, staining and microscopy techniques, or physically removing bound cells and culturing them.

* * * * *